US007841986B2

(12) United States Patent
He et al.

(10) Patent No.: US 7,841,986 B2
(45) Date of Patent: Nov. 30, 2010

(54) METHODS AND APPARATUS OF THREE DIMENSIONAL CARDIAC ELECTROPHYSIOLOGICAL IMAGING

(75) Inventors: Bin He, Arden Hills, MN (US);
Zhongming Liu, St. Paul, MN (US);
Chenguang Liu, St. Paul, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 592 days.

(21) Appl. No.: 11/747,161

(22) Filed: May 10, 2007

(65) Prior Publication Data

US 2007/0270703 A1    Nov. 22, 2007

Related U.S. Application Data

(60) Provisional application No. 60/799,510, filed on May 10, 2006.

(51) Int. Cl.
*A61B 5/0476* (2006.01)

(52) U.S. Cl. ........................................ 600/508; 600/509

(58) Field of Classification Search ................. 600/508, 600/509
See application file for complete search history.

(56) References Cited

U.S. PATENT DOCUMENTS

| 4,961,428 | A | 10/1990 | Nikias et al. |
| 5,311,873 | A | 5/1994 | Savard et al. |
| 5,947,899 | A | 9/1999 | Winslow et al. |
| 6,106,466 | A | 8/2000 | Sheehan et al. |
| 6,240,307 | B1 | 5/2001 | Beatty et al. |
| 6,856,830 | B2 | 2/2005 | He |
| 6,939,309 | B1 | 9/2005 | Beatty et al. |
| 2003/0018277 | A1 | 1/2003 | He |
| 2003/0236466 | A1 | 12/2003 | Tarjan et al. |

FOREIGN PATENT DOCUMENTS

WO     WO00/07501     2/2000

OTHER PUBLICATIONS

Gepstein et al., "A novel method for nonfluoroscopic catheter-based electroanatomical mapping of the heart. In vitro and in vivo accuracy results," *Circulation*, 1997, 95(6):1611-1622.

(Continued)

*Primary Examiner*—Carl H Layno
*Assistant Examiner*—Yun Haeng Lee
(74) *Attorney, Agent, or Firm*—Fish & Richardson P.C.

(57) ABSTRACT

Generating a three-dimensional representation of cardiac electrical activity within a subject's heart includes collecting, from a catheter having a distal portion that includes sensors that sense electrical activity and which catheter distal portion is positioned within a cardiac chamber of a subject, data for electrical activity sensed by the catheter distal portion while positioned within the chamber of the heart. The method also includes executing an imaging algorithm on the collected electrical activity data to generate a three-dimensional representation of cardiac electrical activity within a volume of the subject including all or a portion of the subject's heart. The method further includes displaying the imaged three-dimensional cardiac electrical activity.

26 Claims, 15 Drawing Sheets

OTHER PUBLICATIONS

Hansen, "Truncated singular valve decomposition solutions to discrete ill-posed problems with ill-determined numerical rank," *SIAM J. Sci. Stat. Comput.*, 1990, 11:503-518.

He et al., "Noninvasive three-dimensional activation time imaging of ventricular excitation by means a heart-excitation model," *Phys. Med. Biol.*, 2002, 47:4063-4078.

He, "Imaging and visualization of 3-D Cardiac Electric Activity," *IEEE Trans. Info. Tech. in Biomed.*, 2001, 5(3):181-186.

Jenkins et al., "Multipolar endocardial mapping of the right atrium during cardiac catheterization: description of a new technique," *J. Am. Coll. Cardiol.*, 1993, 22(4):1105-1110.

Li and He, "Localization of the Site of Origin of Cardiac Activation by Means of a heart-Model-Based Electrocardiographic Imaging Approach," *IEEE Trans. Biomed. Eng.*, 2001, 48(6):660-669.

Liu et al., "Noninvasive reconstruction of three-dimensional ventricular activation sequence from the inverse solution of distributed equivalent current density ," *IEEE Trans. Med. Imag.*, 2006, 25(10):1307-1318.

Miller and Geselowitz, "Simulation studies of the electrocardiogram. I. The normal heart," *Circ. Res.*, 1978, 43(2):301-315.

Pascual-Marqui et al., "Low resolution electromagnetic tomography: a new method for localizing electrical activity in the brain," *Int. J. Psychophysiol.*, 1994, 18:49-65.

Tilg et al., "Model-Based Imaging of Cardiac Electrical Excitation in Humans," *IEEE Trans. Med. Imag.*, 2002, 21(9):1031-1039.

Tung, Ph.D. thesis, "A bi-domain model for describing ischemic myocardial d-c potentials," Massachusetts Institute of Technology, 1978.

Zhang et al., "3-Dimensional Activation Sequence Reconstruction from Body Surface Potential Maps by means of a Heart-Model-Based Imaging Approach," *Computers in Cardiology*, 2004, pp. 1-4.

Kosch et al, Institute of Electrical and Electronics Engineers, Non-invasively measured cardiac magnetic field maps improve the estimation of the current distribution, *Computers in Cardiology 2001*, Sep. 23-26, Rotterdam, the Netherlands, XP010573273 pp. 285-288.

METHODS AND APPARATUS OF THREE DIMENSIONAL CARDIAC ELECTROPHYSIOLOGICAL IMAGING

REFERENCE TO RELATED APPLICATIONS

This application claims the benefit of U.S. Provisional Application 60/799,510, filed on May 10, 2006, the contents of which are incorporated by reference herein.

STATEMENT REGARDING FEDERALLY SPONSORED RESEARCH

Work relating to this application was supported in part by grants from the National Science Foundation (BES-0411898 and BES-0411480) and the National Institutes of Health (RO1EB00178). The United States government has certain rights in the invention.

TECHNICAL FIELD

The invention relates to the determination and imaging of the electrical activity of a biological system, such as a heart.

BACKGROUND

Cardiac electrophysiological processes are distributed over the three-dimensional (3-D) volume of the heart. Such processes include excitation and relaxation of the heart. Attempts have been made to probe and image cardiac electrical activity from body surface electrocardiograms or magnetocardiograms, or from catheter recordings within blood cavities, for the purpose of aiding clinical diagnosis and management of cardiac diseases. While the endocardial recordings and non-contact inverse mapping techniques provide a minimally invasive means of localizing and mapping cardiac electrical activity over the endocardial surface, they may be limited when cardiac activation or repolarization inhomogeneity arise or occur from regions far from the endocardial surface.

SUMMARY

Methods, systems, and apparatuses have been developed that utilize cardiac electrophysiological imaging algorithms for use in 3-D imaging of cardiac electrophysiological properties from an array of sensors placed over a catheter being inserted into a blood cavity of an interior chamber of the heart, or an array of electromagnetic sensors placed over or out of the body surface, or a combination of such interior or exterior measurements.

In a first general aspect, a method of generating a three-dimensional representation of cardiac electrical activity within a subject's heart includes collecting, from a catheter having a distal portion with electromagnetic sensors, data arising from cardiac electrical activity sensed by the catheter distal portion while positioned within one or more chambers of the heart. The method also includes executing an imaging algorithm on the collected data to generate a three-dimensional representation of cardiac electrical activity within a volume of the subject including all or a portion of the subject's heart. The method further includes displaying the imaged three-dimensional cardiac electrical activity.

In various implementations, the imaging algorithm may use a source model that represents cardiac electrical activity and estimate the three-dimensional cardiac electrical activity by minimizing the difference between the catheter-recorded data and the source model predicted data. The source model may be a cardiac electrophysiological model constructed based on knowledge of cardiac electrophysiology and geometric measurements of the subject's internal anatomy, including a cellular automaton heart model. The source model may be a heart biophysical model comprising three-dimensional equivalent source representations, including distributed current density, transmembrane potential, extracellular potential, intracellular potential, or various combinations of these physical representations, or their features in space or in time such as activation time, repolarization time and action potential duration. In some implementations, the heart biophysical source model may be a three-dimensional distributed equivalent current density model, and the activation time and repolarization time may be estimated from the local maxima in the time course of the inversely computed equivalent current density at each location in the heart volume.

In various implementations, the geometries of heart and torso of the subject may be obtained from an anatomy imager such as magnetic resonance imaging, computer tomography, ultrasound and fluorescent imaging, and a realistic-geometry heart-torso model may be constructed prior to the three-dimensional cardiac electrical imaging. The imaged three-dimensional representation of the cardiac electrical activity may be displayed within the heart volume of the subject, including all or a portion of the subject's heart, together with the heart anatomy as determined from the anatomy imager. The visual display may include both a time sequence of the cardiac electrical activity at multiple locations and spatial images of the cardiac electrical activity coregistered to the heart anatomy of the subject. The displayed cardiac electrical activity may be both within the three-dimensional volume of the heart and over the endocardial as well as epicardial surface of the heart.

In various implementations, the cardiac electrical activity may be generated during cardiac activation and/or cardiac repolarization. The imaged three-dimensional cardiac electrical activity or its various features in space and/or in time may be used to guide catheter ablation of cardiac arrhythmias or cardiac synchronized therapy of cardiac diseases.

In a second general aspect, a system for generating a three-dimensional representation of cardiac electrical activity within a subject's heart includes a catheter having a distal portion that includes sensors that sense electrical activity. The catheter distal portion is positioned within a cardiac chamber of a subject. The system also includes an amplifying and processing unit that amplifies and filters the sensed electrical signals by the catheter. The system further includes a computation unit that processes the collected data to generate a three-dimensional representation of cardiac electrical activity within a volume of the subject, including all or a portion of the subject's heart. The system further includes a displaying unit to display the imaged three-dimensional cardiac electrical activity.

In various implementations, the computation unit may perform computations to estimate the three-dimensional cardiac electrical activity by minimizing the difference between the catheter collected electrical activity data and a heart source model predicted electrical activity data at the same locations of the sensors in the catheter. The imaged three-dimensional cardiac electrical activity may be used to guide catheter ablation of cardiac arrhythmias or cardiac synchronized therapy of cardiac diseases.

In a third general aspect, a method of generating a three-dimensional representation of cardiac electrical activity within a subject's heart includes collecting, from a catheter having a distal portion comprising sensors that sense electrical activity and which catheter distal portion is positioned within a cardiac chamber of a subject, data for electrical activity sensed by the catheter distal portion while positioned within the chamber of the heart. The method also includes collecting, from an electrode array positioned on the subject's body surface, data for electrical activity sensed by the body surface electrode array taken during a time period during which the electrical activity data collected by the catheter is sensed. The method further includes executing an imaging algorithm using both the electrical activity data collected using the catheter and the electrical activity data collected using the body surface electrode array, to generate a three-dimensional representation of cardiac electrical activity within a volume of the subject including all or a portion of the subject's heart.

In various implementations, the cardiac electrical activity may be generated during cardiac activation and/or cardiac repolarization. The cardiac electrical activity may be generated based on the derived parameters of both activation and repolarization processes. The imaged three-dimensional cardiac electrical activity may be used to guide catheter ablation of cardiac arrhythmias or guide cardiac synchronized therapy.

In a fourth general aspect, a method of generating a three-dimensional representation of cardiac electrical activity within a subject's heart includes collecting electrical activity data using multiple sensors to detect cardiac electrical activity for a subject. The method also includes executing an imaging algorithm on the collected data using the multiple sensors to generate a three-dimensional representation of cardiac electrical activity within a volume of the subject including all or a portion of the subject's heart. The imaging algorithm uses a heart biophysical source model that represents cardiac electrical activity by three-dimensional equivalent current density distribution, estimates the three-dimensional equivalent current density distribution by reducing a difference between the electrical activity data from the multiple sensors and data predicted by the heart biophysical source model at the locations of the multiple sensors, and determines an activation time and a repolarization time from a time course of an equivalent current density at each location within the heart. The method further includes displaying the three-dimensional representation of the cardiac electrical activity.

In various implementations, the electrical activity data may be collected using an array of electrode sensors positioned on the body surface of the subject. The electrical activity data may be collected using an array of magnetic sensors positioned out of the subject. The three-dimensional representation of the cardiac electrical activity may be displayed within the heart volume of the subject, including all or a portion of the subject's heart, together with the heart anatomy as determined from an anatomy imager such as magnetic resonance imaging, computer tomography, ultrasound, fluorescent imaging, in the time domain in the form of waveforms of the estimated cardiac electrical activity at a single or multiple sites within the heart, and/or in the space domain in the form of spatial images coding cardiac electrical activity by color or other forms, at a single time instant or sequentially over a time period. A repolarization dispersion may be further derived and imaged from the estimated equivalent current density to aid in diagnosis and management of cardiovascular diseases.

In a fifth general aspect, an apparatus for generating a three-dimensional representation of cardiac electrical activity within a subject's heart includes multiple sensors to detect cardiac electrical activity for a subject. The apparatus also includes an amplifying and processing unit which amplifies and filters detected electrical activity data by the multiple sensors. The apparatus further includes a computation unit to execute an imaging algorithm on the data using the multiple sensors to generate a three-dimensional representation of cardiac electrical activity within a volume of the subject including all or a portion of the subject's heart. The imaging algorithm uses a heart biophysical source model that represents cardiac electrical activity by three-dimensional equivalent current density distribution, estimates the three-dimensional equivalent current density distribution by reducing the difference between the electrical activity data from the multiple sensors and data predicted by the heart biophysical source model using the three-dimensional equivalent current density distribution at the same locations of the multiple sensors, and determines an activation time and a repolarization time from a time course of the equivalent current density at each location within the heart. The apparatus further includes a displaying unit that displays the three-dimensional representation of the cardiac electrical activity.

In a sixth general aspect, a method for recording electrical activity within a three-dimensional volume within a chamber of a heart includes placing a distal portion of a catheter into a chamber of a heart and recording electrical activity of the heart from multiple locations using a plurality of sensors that occupy a three-dimensional volume within the chamber, the sensors attached to the catheter and immersed in intra-cavity blood of the heart. The method also includes displaying three-dimensional electrical recordings within a chamber of the heart using the recorded electrical activity.

In various implementations, the three-dimensional electrical recordings may be used to estimate and image cardiac electrical activity within the three-dimensional heart or over a heart surface by reducing differences between the recorded three-dimensional electrical recordings and model-predicted electrical data at locations of the sensors.

In a seventh general aspect, an apparatus for recording electrical activity produced by a heart includes a plurality of sensor leads attached to a distal portion of a catheter, each of the plurality of sensor leads including a plurality of electrical activity sensors to detect cardiac electrical activity. The apparatus also includes a control unit to enable the plurality sensor leads to be erected from the distal portion of the catheter to cover a three-dimensional volume within intra-cavity blood, and one or more sensors for sensing geometric locations to determine positions of the electrical activity sensors.

In an eighth general aspect, an apparatus for generating a representation of cardiac electrical activity within a subject's heart includes multiple sensors located within a three-dimensional volume of a chamber of the heart to detect cardiac electrical activity for a subject. The apparatus also includes a processing unit that amplifies and filters electrical activity data detected by the multiple sensors. The apparatus further includes a computation unit that executes an imaging algorithm on the data using the multiple sensors to generate a representation the cardiac electrical activity within a volume of the subject including all or a portion of the subject's heart, wherein the imaging algorithm uses a heart source model that represents cardiac electrical activity, estimates the cardiac electrical activity by reducing a difference between the electrical activity data from the multiple sensors and data predicted by the heart source model at locations of the multiple sensors, and determines an activation time and a repolarization time within the heart. The apparatus further includes a displaying unit that displays a representation of the cardiac electrical activity In another general aspect, the intra-cavity electrical recordings may be made by a catheter consisting of multiple sensor leads which can be controlled to preset positions covering a 3-D volume within the intra-cavity blood. Such catheter thus may record electrical signals at multiple locations covering a volume, instead of only over a surface. Such 3-D intra-cavity electrical recordings will then be used to estimate and image cardiac electrical activity within the 3-D volume of a heart.

In various implementations, the three-dimensional representation of the cardiac electrical activity may be displayed within the heart volume of the subject, including all or a portion of the subject's heart, together with the heart anatomy as determined from an anatomy imager, such as magnetic resonance imaging, computer tomography, ultrasound, fluorescent imaging, in the time domain in the form of waveforms of the estimated cardiac electrical activity at a single or multiple sites within the heart, and/or in the space domain in the form of spatial images coding cardiac electrical activity by color or other forms, at a single time instant or sequentially over a time period. The imaged three-dimensional cardiac electrical activity may be used to guide catheter ablation of cardiac arrhythmias.

DETAILED DESCRIPTION

Methods, systems, and apparatuses have been developed to image three-dimensional (3-D) cardiac electrical activity from sensor arrays within and out of the heart using a cardiac electrophysiological imaging algorithm. Some implementations may include the following methods, systems and apparatuses for 3-D imaging of cardiac electrophysiological properties.

3-D Cardiac Electrophysiological Imaging from Intra-Cavity Biosignals

Figure 1:
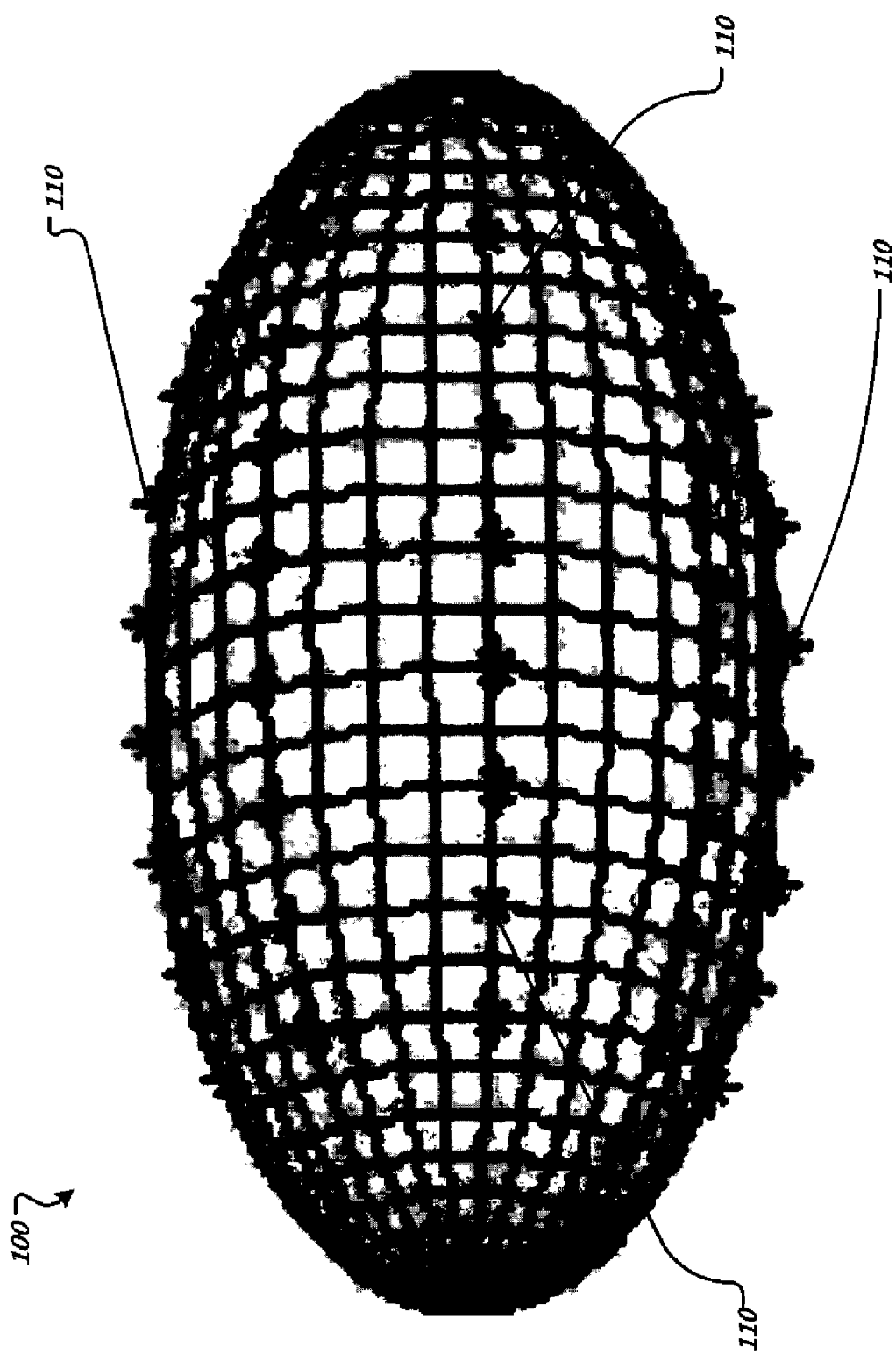
FIG. 1 is a balloon portion of a balloon catheter, with electrode sensors embedded over the balloon portion surface.

In some embodiments, cardiac electrical activity may be sensed by multiple electrode sensors placed within the blood cavity inside of the heart. The cardiac electrical activity can be imaged from such recorded intra-cavity biosignals and an electrophysiological imaging algorithm. Such intra-cavity biosignals can include electrical signals measured by means of a balloon catheter with an array of electric sensors over the catheter (e.g. see U.S. Pat. No. 6,939,309). The intra-cavity biosignals can also include signals measured using a basket catheter consisting of multiple electrodes being attached to the endocardium (e.g., Jenkins et al., 1993). The intra-cavity biosignals may include signals measured using an electroanatomic catheter in a sequential manner (Gepstein et al., 1997). The intra-cavity biosignals may also include signals measured using a catheter with 3-D electrode arrays. The intra-cavity biosignals may be electrical potentials measured in reference to a reference point or a combination of electrical potentials at multiple locations (such as the Wilson Central Terminal), or bipolar recordings which are the difference of electrical potentials at these two points, or multiple leads which are a combination of electrical potentials at the multiple locations. FIG. 1 illustrates a balloon 100 of a balloon catheter (not shown) with multiple electrode sensors 110 over the balloon's surface.

Cardiac electrophysiological imaging (CEI) from intra-cavity biosignals may be used to estimate the 3-D distribution of cardiac electrical activity by minimizing the difference between the recorded and model-generated biosignals at multiple locations within the intra-cavity volume at any instant or during a period of time. Mathematically, the inverse imaging solution J(t) within the 3-D myocardium may be expressed as:

$$\hat{J}(t) = \arg\min_{J(t)} \left( \sum_{t=T_1}^{T_2} \|\Phi_{rec}(t) - \Phi_{model}(t)\|_{k_1}^{l_1} + \lambda(t) \|WJ(t)\|_{k_2}^{l_2} \right) \quad (1)$$

where J(t) is the source distribution, $\Phi_{rec}$ and $\Phi_{model}$ are the recorded and model-generated biosignals at multiple locations within the intra-cavity volume. $k_1$, $k_2$, $l_1$ and $l_2$ are parameters to determine the specific procedures of an inverse imaging solution. ($T_1$, $T_2$) refers to a period during which the inverse imaging is performed, where $T_1$ may be equal to $T_2$ for instantaneous imaging. W is a weighting function, and λ(t) is a regularization parameter. $\Phi_{model}$ can be obtained by solving the forward problem from the cardiac electrical sources J(t) to the intra-cavity biosignals. Some embodiments of the proposed 3-D CEI from intra-cavity biosignals consist of the following exemplary steps. Biosignals can be collected at multiple sites within the intra-cavity volume by a catheter at a time point or over a period of time. Recording electrodes may be positioned within the intra-cavity volume. Geometry information of the heart and torso can be obtained by, for example, magnetic resonance imaging (MRI), computer tomography (CT), ultrasound imaging and fluorescent imaging. The forward procedure can be solved to calculate the intra-cavity biosignals at the recording sites from cardiac sources. The inverse procedure can be solved to estimate 3-D cardiac electrical activity from the recorded intra-cavity biosignals. Cardiac electrophysiological properties of myocardial tissue, such as the activation time, repolarization time, transmembrane potential, action potential duration, or other properties of cardiac activation and repolarization may be derived from the inverse solutions. Imaging results can be displayed with or without other imaging results. The estimated site(s) of initiation of arrhythmias or reentrant circuits may be ablated and the outcome of the ablation can be estimated by reapplying the imaging procedures. The 3-D cardiac electrical activity estimated may also be used to guide cardiac synchronized therapy.

Figure 2A:
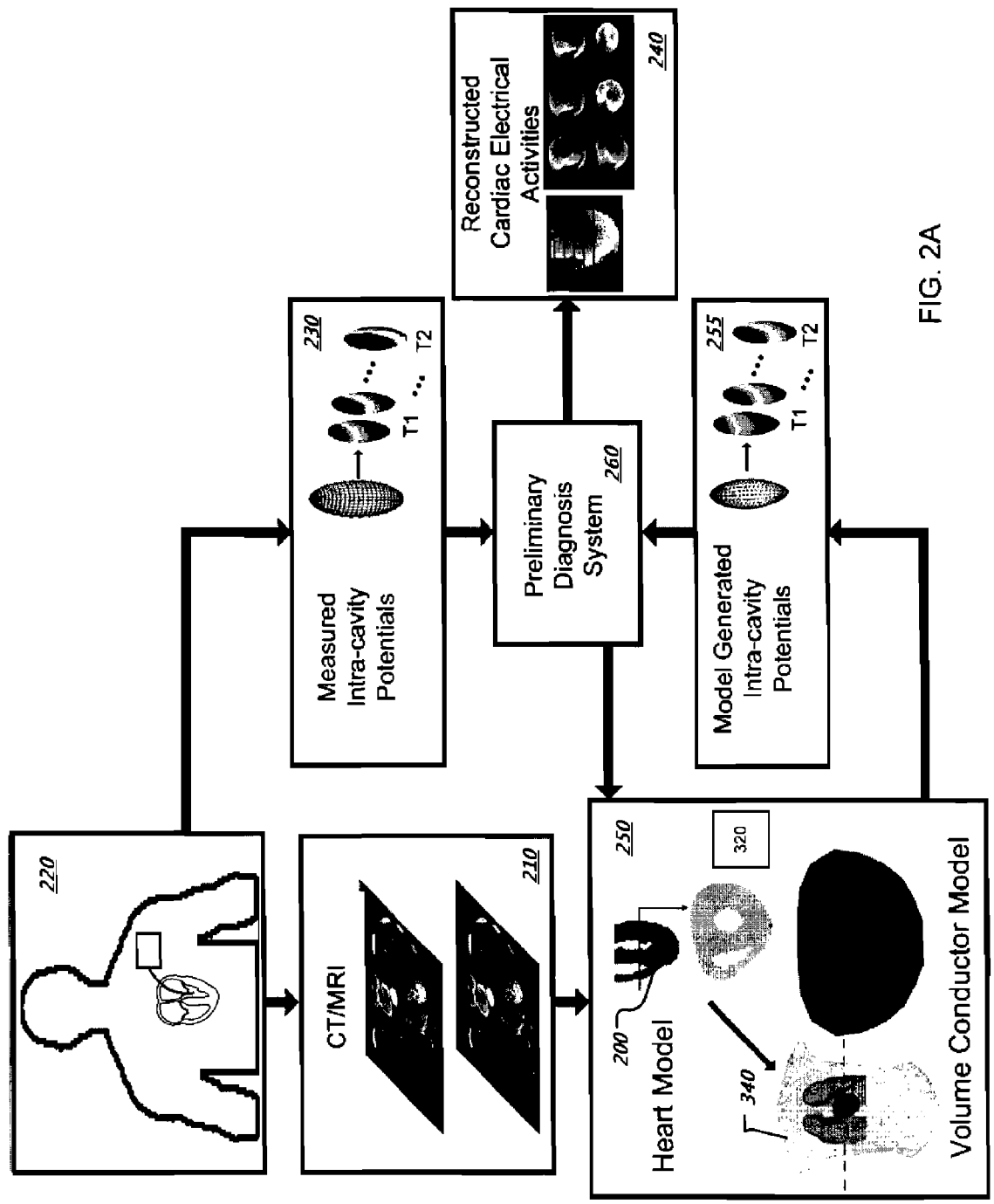
FIG. 2A is an illustration of a method of performing 3-D cardiac electrophysiological imaging from intra-cavity potentials.
Figure 2B:
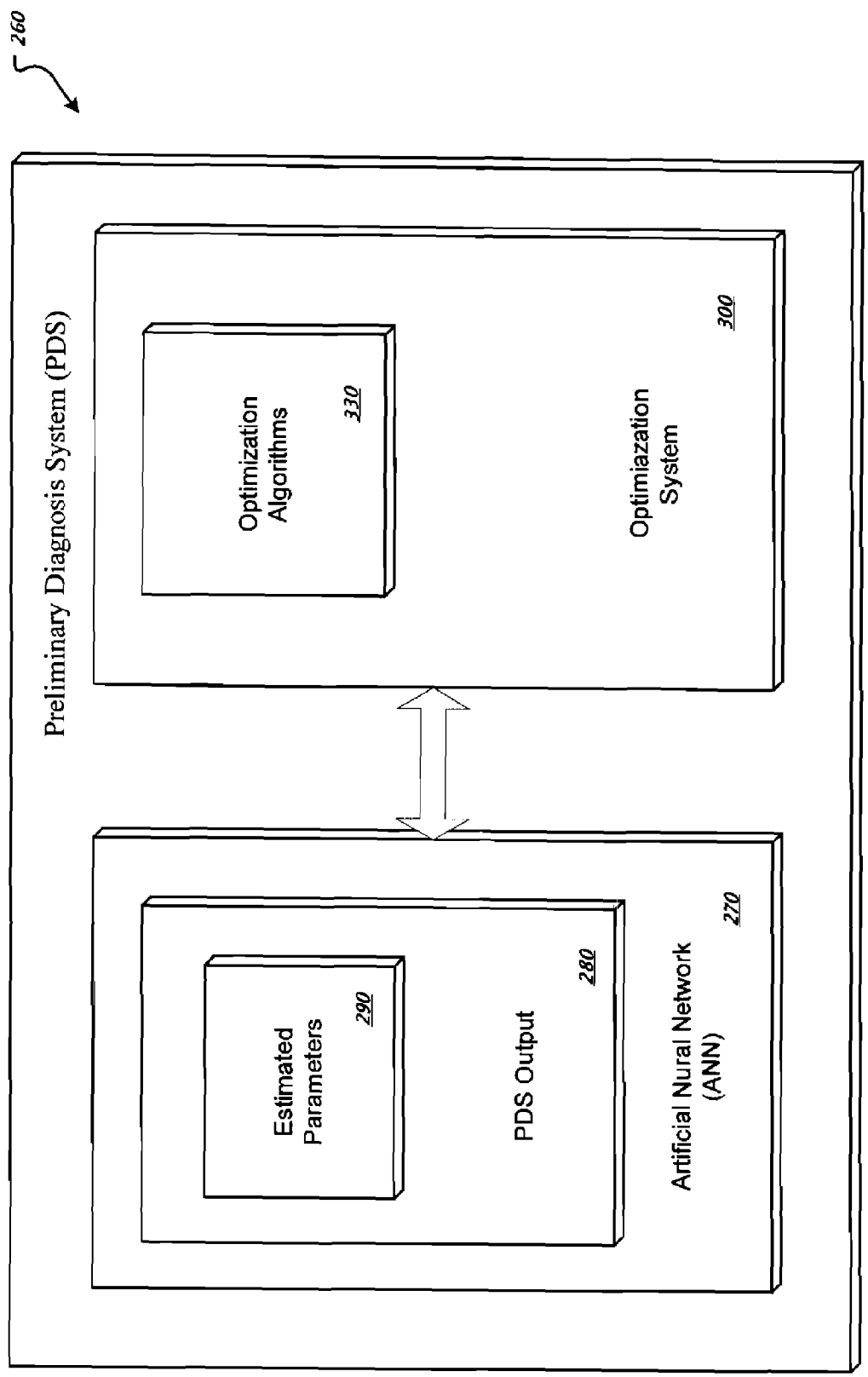
FIG. 2B is a block diagram of a diagnosis system shown in FIG. 2A.

Referring to FIGS. 2A-2B, in some embodiments, the inverse imaging can be accomplished through the use of a 3-D heart electrophysiological model 200. The heart electrophysiological model 200 (e.g., a cellular-automaton heart model) may be constructed based on general knowledge of cardiac electrophysiology and geometric measurements 210 (e.g., made via magnetic resonance imaging, computer tomography, or the like) of a patient 220. The patient 220 may have an implanted device that includes a catheter with one or more sensors for taking electrical measurements. Some examples of such a catheter include a balloon catheter having a balloon with sensors thereon (such as shown in FIG. 1) or a catheter of the type described below with respect to FIG. 14. The anisotropic nature of myocardium may be incorporated into the computer heart electrophysiological model 200. A relationship between recorded intra-cavity biosignals 230 at multiple locations and 3-D cardiac electrophysiological properties 240 to be estimated can be established through use of a heart-excitation (or repolarization)—torso-volume-conductor—model (later referred to as a heart-torso-model 250). In some embodiments, the heart-torso-model 250 may be used to generate a set of model generated intra-cavity biosignals 255.

A preliminary diagnosis system (PDS) 260 (shown in greater detail in FIG. 2B) can be employed to determine cardiac status based on the general knowledge of cardiac electrophysiology, the recorded intra-cavity biosignals 230, and the model generated intra-cavity biosignals 255. An artificial neural network (ANN) 270 or other like procedures can be used for realizing this functionality. The PDS output 280 can include the initial estimate of parameters 290 of the heart electrophysiological model 200 being used later in an optimization system 300. The optimization system 300 then minimizes the objective functions that assess the dissimilarity between the measured intra-cavity biosignals 230 and the model-generated intra-cavity biosignals 255. In some examples, if the measured intra-cavity biosignals 230 and the model-generated intra-cavity biosignals 255 match well, the estimated cardiac electrophysiological properties 240 throughout the 3-D volume of heart are determined from heart model parameters 320 corresponding to the recorded intra-cavity biosignals 230. If not, the heart model parameters 320 may be adjusted with the aid of the optimization algorithms 330. The optimization procedure may proceed until the objective functions satisfy given convergent criteria, at which point the cardiac electrophysiological properties 240 throughout the 3-D myocardium can be estimated.

In some embodiments, the artificial neural network (ANN) 270 and the optimization system 300 can be part of the preliminary diagnosis system 260. In alternate embodiments, functions performed by the ANN 270, the optimization system 300, and the PDS 260 can be performed by any combination of elements without affecting the spirit of the procedure described here.

Still referring to FIGS. 2A-2B, in some embodiments, the following objective functions can be used to reflect dissimilarity between the measured intra-cavity biosignals 230 and model-generated intra-cavity biosignals 255: $E_{CC}(x)$, which can be constructed with the average correlation coefficient (CC) between the measured intra-cavity biosignals 230 and model-generated intra-cavity biosignals 255 during a certain time period of cardiac cycle, which may include cardiac excitation or repolarization. In addition, the following two constraints can also be used: (a) $E_{minp}(x)$, which can be constructed with the deviation of the positions of minima of the measured intra-cavity biosignals 230 and model-generated intra-cavity biosignals 255 during a certain time period of cardiac cycle, which may include cardiac excitation or repolarization; (b) $E_{NPL}(X)$, which can constructed with the relative error of the number of recording sensors, at which the biosignals are less than a certain threshold, in the measured intra-cavity biosignals 230 and model-generated intra-cavity biosignals 255 during a certain time period of cardiac cycle, which may include cardiac excitation or repolarization. A mathematical model of the optimization can be represented as the following minimization problem:

$$\min_{x \in X}(E_{CC}(x)) = E^*_{CC}, E_{\min p}(x) < \varepsilon_{\min p}, E_{NPL}(x) < \varepsilon_{NPL} \qquad (2)$$

where x is the probable value region in the computer heart model of the parameters 320; X is a parameter vector of the state in the heart electrophysiological model 200; $E^*_{CC}$ is the optimal value of the objective function $e_{cc}(x)$; and $\epsilon_{minp}$ and $\epsilon_{npl}$ are the allowable errors of the constraints $e_{minp}(x)$ and $e_{npl}(x)$, respectively. The simplex method or other optimization methods can be used solve equation (2).

In one aspect, the forward solution $\Phi_{model}$ of Equation (1) can be obtained by using a numerical method (e.g., finite element method (FEM), boundary element method (BEM), or the like) with the aid of a heart electrophysiolological model 200. In one embodiment, a cellular-automaton heart model can be used to simulate cardiac electrophysiological processes, including activation and repolarization. The heart model can be constructed from a set of myocardial cell units, located at a corresponding cardiac volume at which an action potential is assigned. The anisotropic propagation of excitation in the myocardium can be incorporated into such a computer heart model.

Based on the bidomain theory, the extracellular electrical potential $\Phi$ within the thorax $\Omega$ can be solved from the following:

$$\nabla \cdot [(\sigma_i + \sigma_e) \nabla \phi] = \nabla \cdot J \text{ in } \Omega; \sigma(\nabla \phi) \cdot n = 0 \text{ on } S \qquad (3)$$

$$J = -\sigma_i \nabla V_m \text{ in } \Omega \qquad (4)$$

where $\sigma_i$ and $\sigma_e$ are the intracellular and interstitial conductivity tensor, J the equivalent current density, $V_m$ the transmembrane potential, and n the outward unit normal to the body surface S.

Still referring to FIG. 2A, in some embodiments, a finite element (FE) model 340 can be built to represent the realistic geometry thorax volume conductor from CT/MR images of the torso and heart. The CT/MR images can be segmented, edge-detected, and contoured for the torso, lungs, epicardial and endocardial surfaces, respectively. The surface contours can be meshed by triangles to build a boundary element (BE) model. The BE model of a balloon catheter in an inflated status is embedded into the left ventricle cavity. The triangulated surface models are then transformed to a volume definition model using Non-Uniform Rational B-Splines (NURBS), which may provide an accurate mathematical description of 3-D geometry, in order to generate FE meshes. The FE model 340 can be obtained by meshing the integrated NURBS geometry model. Tetrahedral elements within the myocardium and the blood mass can have finer resolution as compared to other areas. In some implementations, the torso, lungs and blood mass can be assumed to be isotropic conductors, or to have anisotropic distributions of electrical conductivity obtained from diffusion tensor magnetic resonance imaging. The anisotropy of cardiac tissue is incorporated into the computer model. Equation (3) can be discretized into linear equations at each finite element. The linear equations can be solved by the preconditioned conjugate gradients method, or other solvers, to obtain the electrical potential at every FE node.

In some embodiments, the field equations (3)-(4) can be solved by means of the boundary element method assuming isotropic conductivity distribution. The intra-cavity biosignals can be solved from the assumed cardiac sources within the volume conductor.

Figure 3:
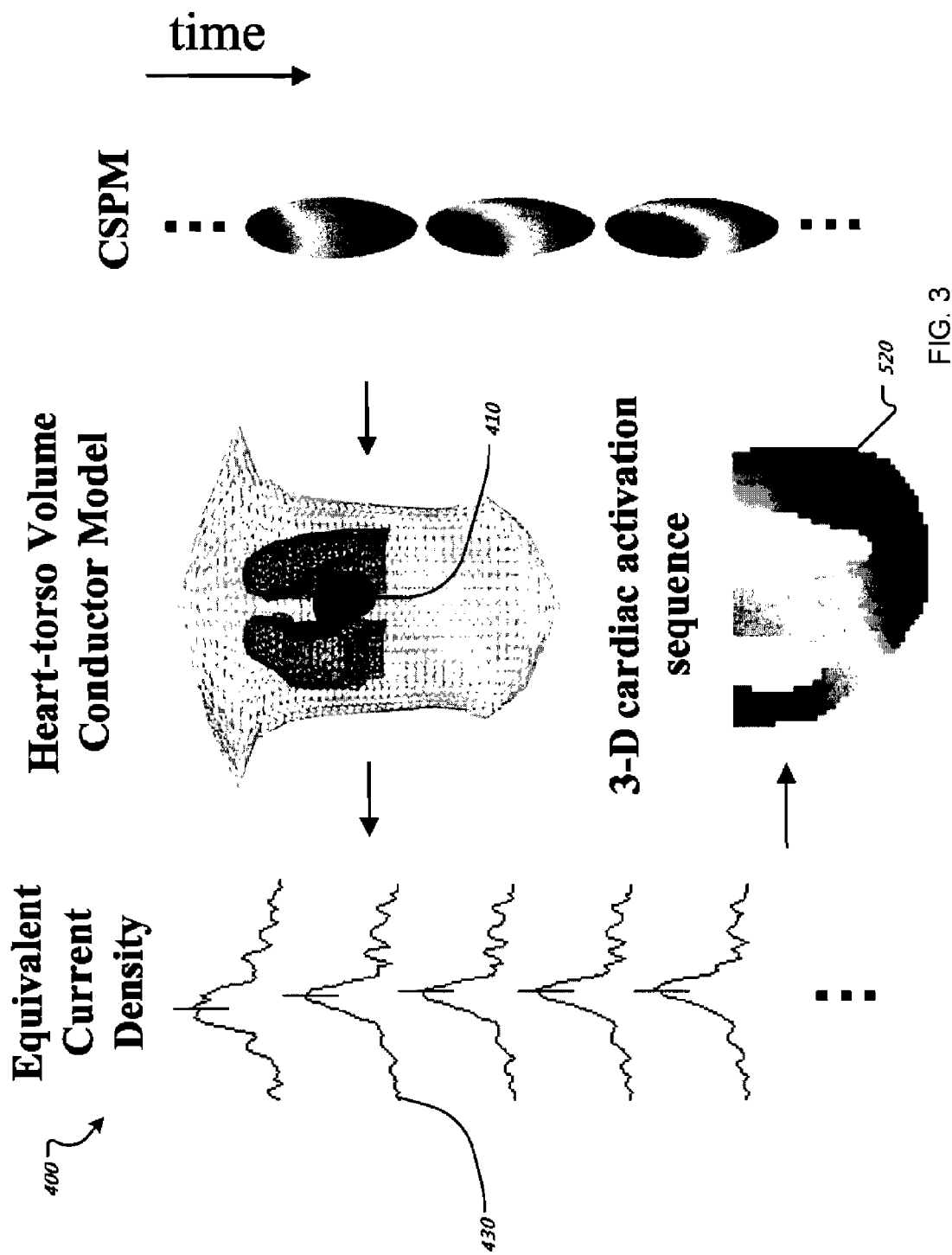
FIG. 3 is an illustration of heart biophysical model based three-dimensional cardiac activation imaging from intra-cavity potentials.

In some embodiments, the inverse imaging can be accomplished by means of a heart biophysical model 400 as shown in FIG. 3. Referring to FIGS. 3-4, the source distribution J(t) in Equation (1) may represent the current density at every possible source location $r_s$ inside a heart volume 410.

According to cardiac biophysics, the amplitude 420 of equivalent current density $\vec{j}_{eq}(r_s,t)$ 430 is proportional to the spatial gradient of a transmembrane potential $\nabla \phi_m(r_s,t)$ 440. If one considers the process of ventricular depolarization (e.g. during the QRS interval), the spatial distribution of $\vec{j}_{eq}(r_s,t)$ 430 can be dominated by its values at the interface, or excitation wavefront 470, between the depolarized myocardium 450 and non-depolarized myocardium 460, where the myocardial cells are undergoing rapid depolarization. These myocardial cells may stay in depolarization phase briefly and thereby the excitation wavefront 470 may be expected to propagate by a given myocardial site at its activation time 480. When looking at the time-varying equivalent current density $\vec{j}_{eq}(r_k,t)$ 430 at a fixed location $r_k$, its amplitude $|\vec{j}_{eq}(r_k,t)|$ 420 may reach a maximum value at its activation time $\tau(r_k)$ 480 during the entire duration $T_d$ of ventricular depolarization. This concept can be mathematically expressed by Eq. (5) and also illustrated in FIGS. 4A-4B.

$$\arg\max_{t \in T_d}\left(\left|\vec{j}_{eq}(r_k, t)\right|\right) = \tau(r_k) \quad (5)$$

The repolarization time $u(r_k)$ 490 may be estimated at another extreme of $\vec{j}_{eq}(r_s,t)$ 430 in the time domain, corresponding to the corner of transition of transmembrane potential from plateau to repolarization:

$$\arg\max_{t \in T_r}\left(\left|\vec{j}_{eq}(r_k, t)\right|\right) = u(r_k) \quad (6)$$

where Tr refers to the entire repolarization duration. The repolarization time $u(r_k)$ 490 may also be estimated by another criterion of the function of $\vec{j}_{eq}(r_s,t)$ 430 during the repolarization duration.

Figure 4A:
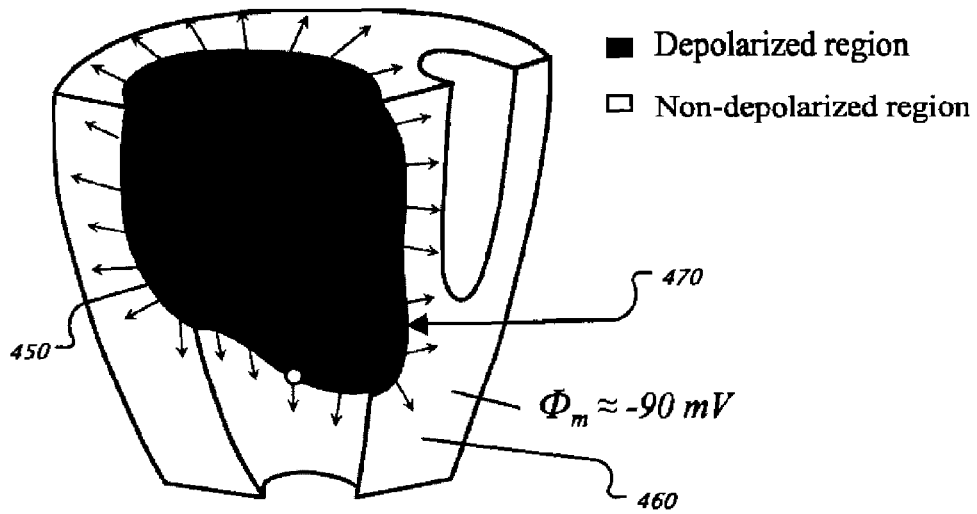
FIG. 4A is a volume of cardiac tissue.
Figure 4B:
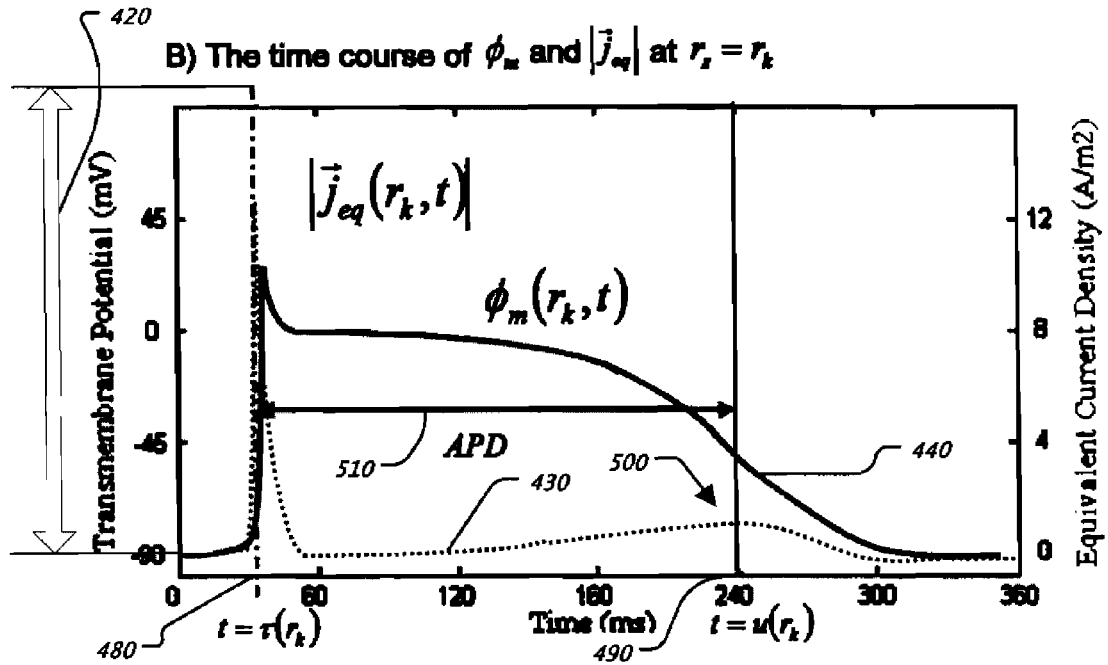
FIG. 4B is a graph of electrical activity for the cardiac tissue of FIG. 4A.

Because the process of repolarization can be slow when compared with the activation, the temporal behavior of the waveform of $\vec{j}_{eq}(r_s,t)$ 430 can show a more diffused peak 500 surrounding the repolarization time $u(r_k)$ 490 as compared to the depolarization time 480. FIGS. 4A-4B illustrate the concept of activation time 480 and repolarization time 490 in the waveform of $\vec{j}_{eq}(r_s,t)$ 430 shown together with the waveform of the transmembrane potential at location $r_k$. The action potential duration (APD) 510 can be estimated from the difference of activation time $\tau(r_k)$ 480 and the repolarization time $u(r_k)$ 490. Furthermore, the repolarization dispersion and inhomogeneity may be estimated from variations of APD 510 and the area under the waveform of $\vec{j}_{eq}(r_s,t)$ 430 surrounding the repolarization time $u(r_k)$ 490.

In some embodiments, an example of which is shown in FIG. 3, the 3-D activation sequence 520 may be estimated from the maximum value of the time waveform of the equivalent current density 430. A similar approach can be applied to obtain repolarization imaging according to Eq. (6) and the method described above.

3-D Cardiac Electrophysiological Imaging from Noninvasive Electromagnetic Signals In some aspects, the cardiac electrical activity may be sensed from an array of electrode sensors placed over the body surface, or from an array of magnetic sensors placed over a surface or a volume out of the body. Such electromagnetic signals may provide noninvasive measurement of the cardiac electrical activity which can be used to image 3-D cardiac electrophysiological properties within the myocardium. The body surface electrical measurements may be electrical potentials recorded by electrodes in reference to a reference point or a combination of electrical potentials at multiple locations (e.g., such as the Wilson Central Terminal). The magnetic measurements may be magnetic field or magnetic flux density or other magnetic quantities produced by the heart, which may be recorded by SQUID or other magnetic sensors at multiple locations out of the body.

A. 3-D Equivalent Current Density

The notion of equivalent current density comes from the bidomain theory (Miller and Geselowitz, 1978; Tung, 1978). It is stated that as far as the calculation of far-field electrical potential is concerned, the discrete cellular architecture can be simplified into a macroscopic continuum model that consists of both intracellular and extracellular domains. These two domains may equally occupy the entire myocardial volume and may be coupled by the continuity of transmembrane currents flowing from one domain to the other across a theoretical membrane of zero thickness. Based on this theory, the electrical field within the heart-torso volume conductor, assuming quasi-static conditions, may be governed by Eq. (7):

$$\nabla \cdot [(G_i+G_e)\nabla\phi_e] = \nabla \cdot (-G_i\nabla\phi_m) \quad (7)$$

where $G_i$ and $G_e$ are the intracellular and extracellular effective conductivity tensors, $\phi_e$ is the extracellular potential, and $\phi_m$ is the transmembrane potential confined to the 3-D myocardial volume, respectively.

If equivalent current density $\vec{j}_{eq}$ is described as Eq. (8):

$$\vec{j}_{eq} = -G_i \nabla \phi_m \qquad (8)$$

then Eq. (7) can be rewritten as follows:

$$\nabla \cdot [(G_i + G_e) \nabla \phi_e] = \nabla \cdot \vec{j}_{eq} \qquad (9)$$

Eq. (9) suggests that $\vec{j}_{eq}$ can serve as equivalent current sources, replacing the actual ionic currents, for computing the field potential generated by cardiac electrical activity. At any instant t, an electrical potential $\phi_b$ at an observation point $r_b$ over the torso surface can be expressed as a linear superimposition of instantaneous potential fields generated by equivalent sources $\vec{j}_{eq}$ at every possible source location $r_s$ inside the heart volume V, as Eq. (10):

$$\phi_b(r_b, t) = \int_{r_s \in V} \vec{\Psi}_\phi(r_b, r_s) \cdot \vec{j}_{eq}(r_s, t) \, dr_s^3 \qquad (10)$$

where the impendence transfer function $\vec{\Psi}_\phi(r_b, r_s)$ may be dependent on the electrical conductivities and shape of the heart-torso volume conductor.

Similarly, the magnetic flux density of the heart $\vec{B}_b$ at an observation point $r_b$ out of the body, at any instant t, can be expressed as a linear superimposition of the instantaneous magnetic fields generated by the equivalent sources $\vec{j}_{eq}$ at every possible source location $r_s$ inside the heart volume V, as Eq. (11):

$$\vec{B}_b(r_b, t) = \int_{r_s \in V} \vec{\Psi}_B(r_b, r_s) \times \vec{j}_{eq}(r_s, t) \, dr_s^3 \qquad (11)$$

where the impendence transfer function $\vec{\Psi}_B(r_b, r_s)$ is dependent on the electrical conductivities, and shape of the heart-torso volume conductor.

B. Electrophysiological Imaging Based On Equivalent Current Density

According to the cardiac biophysics, the amplitude 420 of the equivalent current density $\vec{j}_{eq}(r_s, t)$ 430 is proportional to the spatial gradient of the transmembrane potential $\nabla \phi_m(r_s, t)$ 440. If one considers the process of ventricular depolarization (e.g. during the QRS interval), the spatial distribution of $\vec{j}_{eq}(r_s, t)$ 430 is dominated by its values at the interface, or excitation wavefront 470, between the depolarized myocardium 450 and the non-depolarized myocardium 460, where the myocardial cells are undergoing rapid depolarization. These myocardial cells may stay in depolarization phase briefly, and thereby the excitation wavefront 470 is expected to propagate by a given myocardial site at its activation time 480. Looking at the time-varying equivalent current density $\vec{j}_{eq}(r_k, t)$ 430 at a fixed location $r_k$, its amplitude $|\vec{j}_{eq}(r_k, t)|$ 420 reaches the maximum value exactly at its activation time $\tau(r_k)$ 480 during the entire duration Td of ventricular depolarization. This concept is mathematically expressed by Eq. (5). Similarly, the repolarization time 490 may be estimated at another extrema of $\vec{j}_{eq}(r_s, t)$ 430 in the time domain, corresponding to the corner of transition of transmembrane potential from plateau to repolarization, as illustrated by equation (6).

The temporal behavior of the waveform of $\vec{j}_{eq}(r_s, t)$ shows a more diffused peak surrounding the repolarization time $u(r_k)$ as compared to the depolarization time. FIG. 4A-4B illustrate the concept of activation time and repolarization time in the waveform of $\vec{j}_{eq}(r_s, t)$ 430 in corresponding to the transmembrane potential 440 at location $r_k$. The action potential duration APD 510 can be estimated from the difference of activation time $\tau(r_k)$ 480 and the repolarization time $u(r_k)$ 490. Furthermore, the repolarization dispersion and inhomogeneity may be estimated from variation of APD 510 and the area under the waveform of $\vec{j}_{eq}(r_s, t)$ surrounding the repolarization time $u(r_k)$ 490. The repolarization time $u(r_k)$ 490 can also be estimated by another criterion of the function of $\vec{j}_{eq}(r_s, t)$ 430 during the repolarization duration.

The such derived activation time may represent a noninvasive alternative estimate the invasive recordings of local activation time using a bipolar electrode. The activation time at a given myocardial location is considered to be at the time instant when the negative first temporal derivative of the electrical potential reaches the maximum value. It has also been shown that the bipolar electrode, which essentially represents the first spatial derivative of the electrical potential, can estimate the activation time, and used in investigating sustained or non-sustained ventricular tachycardia with focal or re-entry mechanism. The present means of estimating the activation time from the equivalent current density estimate, represents a noninvasive realization of the estimation of the spatial derivative of the electric potential. This aspect of the activation time estimation shall also be true for the repolarization time estimation.

Furthermore, the estimated activation time can also be subject to a 3-D Laplacian operator. The negative 3-D spatial Laplacian of activation time distribution may be able to characterize the locations of infarction or abnormal slow conduction due to ischemia, or other abnormal cardiac conduction. Non-zero 3-D curl of gradient of activation time may be able to characterize the re-entry circuits. Thus spatio-temporal features of imaged activation (or repolarization) times may be derived to localize the site of myocardial infarction/ischemia or to detect the re-entry circuits.

C. Noninvasive Electrophysiological Imaging

Figure 5:
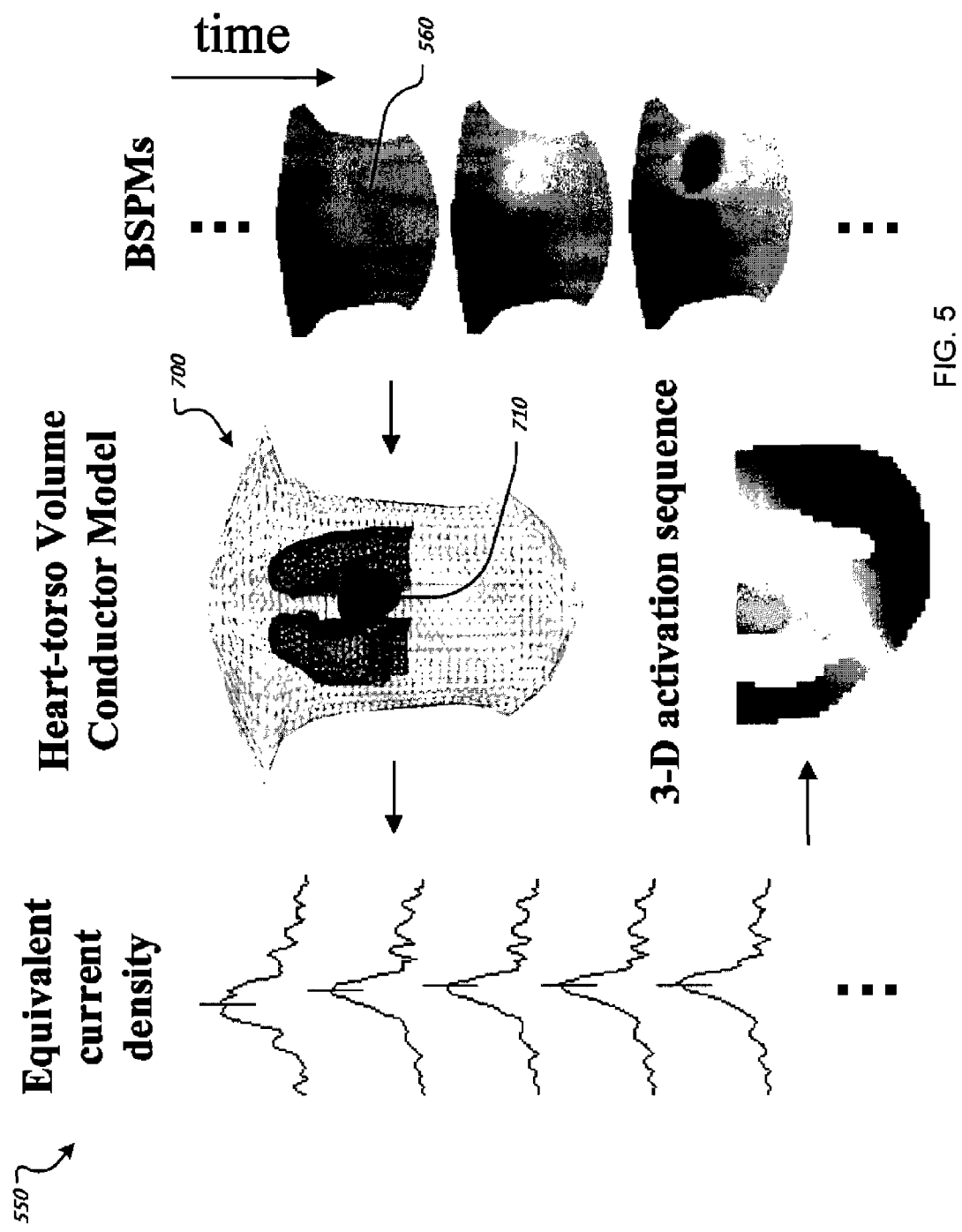
FIG. 5 is an illustration of heart biophysical model based three-dimensional cardiac activation imaging from body surface potentials.

Eq. (5) and Eq. (6) indicate that the activation time and repolarization time throughout the 3-D myocardial volume can be estimated by evaluating the time course of local equivalent current density at every myocardial site. Noninvasive estimation of an activation sequence or repolarization process of the heart from noninvasive electromagnetic measurements may consist of modeling and imaging 3-D equivalent current sources and detecting temporal "markers" at which inversely calculated source magnitude arrives at local maximal peaks. FIG. 5 illustrates the idea of the proposed 3-D activation imaging method 550, using body surface potential maps (BSPMs) 560. This approach may be applicable to magnetic recordings, and hybrid recordings consisting of electrical and magnetic recordings. Similarly, such an approach can be applied to repolarization imaging or other 3-D cardiac electrical imaging as described above.

In exemplary implementations, the myocardium can be divided into N grid points, to model the distributed current sources. At each grid point, an orthogonal triple of dipoles can be placed to represent the vector field of local equivalent current density with arbitrary direction. After discretization of relevant surfaces that separate the torso, lungs, heart and blood cavity, applying the boundary element method (BEM) may yield a discrete matrix equation as Eq. (12) in place of Eq. (10). This equation can be used to solve the forward problem of calculating the body surface potentials $\Phi_b(t)$ at M electrode positions from the equivalent current sources $J(t)$ at N known myocardial sites for any time instant t.

$$\Phi_b(t) = L_\phi J(t) \tag{12a}$$

where $L_\phi = (L_1, L_2, \ldots, L_N)$ is an M×3N transfer matrix, and $L_i$ is an M×3 matrix that represents the electric lead field of the three orthogonal source components at the i-th grid point. Similarly, Eq. (11) can be discretized and a linear equation system can be obtained to replace Eq. (11):

$$B_b(t) = L_B J(t) \tag{12b}$$

where $B_b(t)$ is a quantity corresponding to the magnetic recording using the magnetic sensors and $L_B$ is the transfer matrix that represents the magnetic lead field of the three orthogonal source components at the i-th grid point. Mathematical regularization can be used to obtain a unique and stable solution.

The inverse problem of (12a) from body surface electrical potentials can be solved by means of the following constrained regularization:

$$\arg\min_{J(t)} \left( \sum_{t=T_1}^{T_2} \|\Phi_b(t) - L_\phi J(t)\|_{k_1}^{l_1} + \lambda(t)\|WJ(t)\|_{k_2}^{l_2} \right) \tag{13a}$$

where W is a 3N×3N regularization matrix and $\lambda$ is the regularization parameter. $k_1$, $k_2$, $l_1$ and $l_2$ may be parameters to determine the specific procedures of an inverse imaging solution. $(T_1, T_2)$ may refer to a period during which the inverse imaging is performed, where $T_1$ maybe equal to $T_2$ for instantaneous imaging.

Similarly, the inverse problem of (12b) from magnetic recordings can be solved by means of the following constrained regularization:

$$\arg\min_{J(t)} \left( \sum_{t=T_1}^{T_2} \|B_b(t) - L_B J(t)\|_{k_1}^{l_1} + \lambda(t)\|WJ(t)\|_{k_2}^{l_2} \right) \tag{13b}$$

where W is a 3N×3N regularization matrix and $\lambda$ is the regularization parameter. $k_1$, $k_2$, $l_1$ and $l_2$ may be parameters to determine the specific procedures of an inverse imaging solution. $(T_1, T_2)$ may refer to a period during which inverse imaging is performed, where $T_1$ maybe equal to $T_2$ for instantaneous imaging.

Cardiac Field Potential Imaging

In some embodiments, transmembrane, extracellular and/or intracellular potentials in the 3-D myocardial volume can be imaged from a set of intra-cavity biosignals, body surface biosignals, or magnetic signals using arrays of electrical or magnetic sensors. According to the bidomain theory (Miller and Geselowitz, 1978; Tung, 1978), the electrical field within the heart-torso volume conductor, assuming quasi-static conditions, is governed by Eq. (7). Furthermore:

$$\Phi_m = \Phi_i - \Phi_e \tag{14}$$

where $\phi_i$ and $\phi_e$ are the intracellular and extracellular potential, respectively.

From Eqs. (7) and (14), a linear relationship between the electrical potential measurements can be derived at multiple locations within the torso volume conductor $\Phi_b(t)$ and the cardiac transmembrane, extracellular or intracellular potentials, in discretized version $$\Phi_b(t) = L_m \Phi_m(t) \tag{15a}$$

$$\Phi_b(t) = L_i \Phi_i(t) \tag{15b}$$

$$\Phi_b(t) = L_e \Phi_e(t) \tag{15c}$$

where $L_m$, $L_i$, and $L_e$ are transfer matrices corresponding to the transmembrane, extracellular or intracellular potentials, respectively.

Similarly, the linear relationship between the magnetic measurements at multiple locations out of the body $B_b(t)$ and the cardiac transmembrane, extracellular or intracellular potentials, can be obtained, in discretized version $$B_b(t) = L_{bm} \Phi_m(t) \tag{16a}$$

$$B_b(t) = L_{bi} \Phi_i(t) \tag{16b}$$

$$B_b(t) = L_{be} \Phi_e(t) \tag{16c}$$

where $L_{bm}$, $L_{bi}$, and $L_{be}$ are transfer matrices corresponding to the transmembrane, extracellular or intracellular potentials, respectively.

Mathematical regularization may be necessary to obtain a unique and stable solution to the inverse problem of equations (15a,b,c) and (16a,b,c). The constrained regularization of (13a,b) can be used to solve equations (15a,b,c) and (16a,b,c).

Cardiac Hybrid Electromagnetic Imaging

Figure 6:
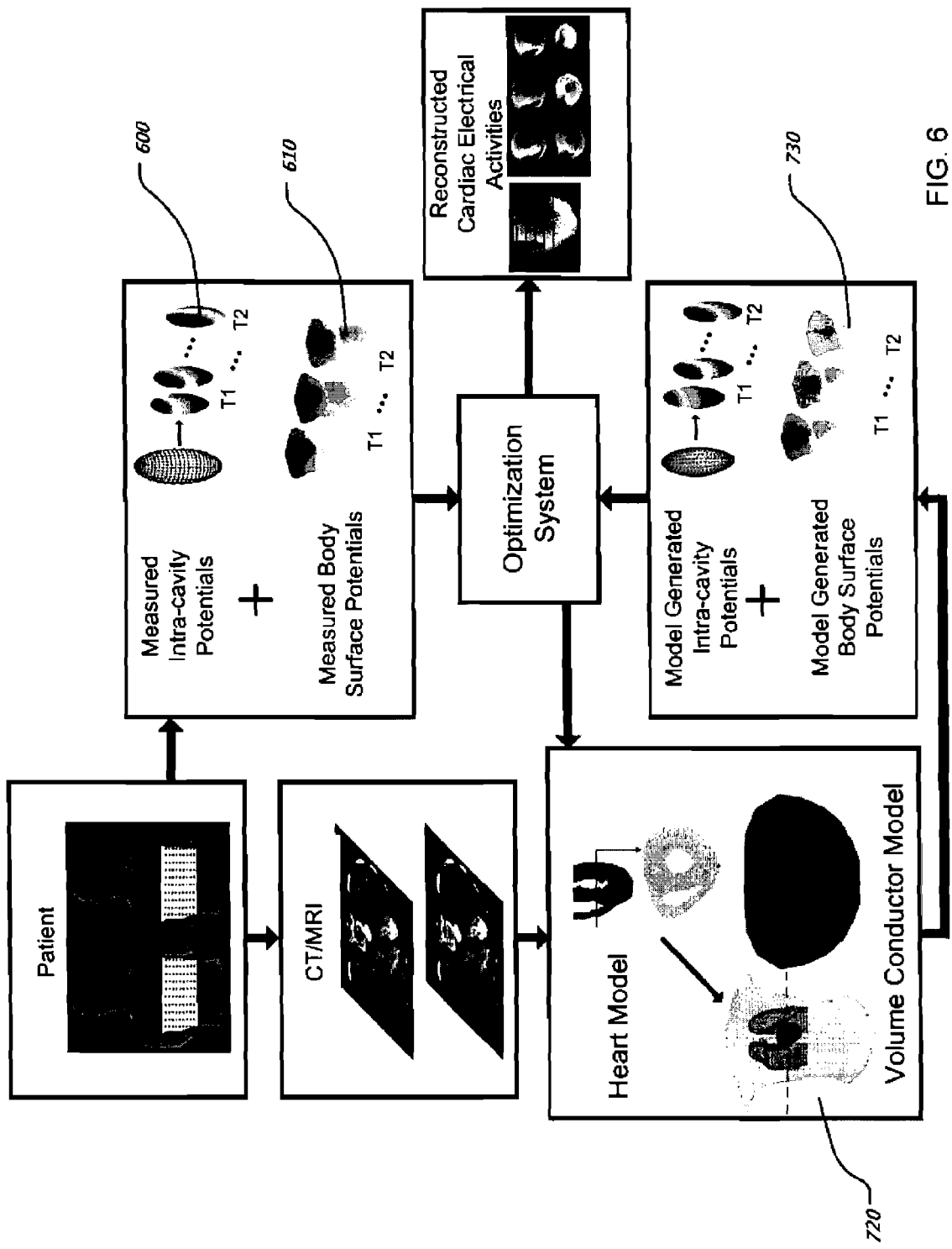
FIG. 6 is an illustration of a method of performing 3-D cardiac electrophysiological imaging from both intra-cavity potentials and body surface potentials.

In some embodiments, cardiac electrophysiological imaging can be performed using hybrid recordings from both intra-cavity biosignals and body surface biosignals. Cardiac electrical activity including an activation process and a repolarization process may be imaged from electrical recordings made at multiple sites from both inside and outside of the heart, according to some implementations. Such an aspect may apply to previously described imaging methods, including but not limited to 3-D activation imaging, repolarization imaging, transmembrane potential imaging, intracellular potential imaging, extracellular potential imaging, and cardiac source imaging. FIG. 6 illustrates an exemplary implementation which uses both intra-cavity biosignals 600 and body surface biosignals 610 for cardiac electrophysiological imaging.

In some implementations, cardiac electrophysiological imaging can be performed using hybrid recordings from both electrical and magnetic sensor arrays. Cardiac electrical activity, including activation process activity and repolarization process activity may be imaged from the electrical and magnetic recordings by integrating the measurements. Such an aspect may apply to imaging methods previously described, including but not limited to 3-D activation imaging, repolarization imaging, transmembrane potential imag-

Example 1

Constrained Regularization Solution of Cardiac Linear Inverse Problem

In some examples, the constrained regularization of equation (13a) may be solved using an inverse solution from instantaneous body surface electrical potentials (that is, a linear inverse operator when $T_1=T_2$). The similar algorithms can be applicable to solve other inverse problems using magnetic signals and intra-cavity biosignals, such as equations (1), (13b), (15,a,b,c), (16a,b,c).

A solution to equation (13a) can be given when $T_1=T_2$:

$$H(\lambda)=(W^TW)^{-1}L^T(L(W^TW)^{-1}L^T+\lambda I)^{-1} \qquad (17)$$

where $L=L_\phi$ when imaging cardiac electrical activity from body surface electrical potentials, $L=L_B$ when imaging cardiac electrical activity from magnetic recordings, or L is equal other transfer matrices $L_m$, $L_i$, $L_e$ $L_{bm}$, $L_{bi}$, and $L_{be}$, as shown in equations (15a,b,c) and (16a,b,c).

For the weighting matrix W, we consider two different settings. When W=I (I denotes an identity matrix), Eq. (17) leads to a minimum norm (MN) solution, which is a 3-D current density distribution with the least instantaneous power among all the possible solutions that are compatible to the measurements. A weighted minimum norm (WMN) solution utilizes $W=\Omega \otimes I$ ($\otimes$ denotes the Kronecker product, I is the 3×3 identity matrix, and $\Omega$ is an N×N diagonal matrix) (Pascual-Marqui et al., 1994). $\Omega$ provides a single normalization factor for all three dipole components at each grid point. More specifically, the normalization factor for the i-th grid point may be calculated as the norm of its corresponding lead field $L_i$ (either electrical or magnetic lead field), as Eq. (18):

$$\Omega_{ii} = \sqrt{\sum_{j=1}^{3} L_{ij}^T L_{ij}} \qquad (18)$$

Weighting matrixes other than those mentioned above may also be used.

The regularization parameter $\lambda$ can be determined by the "L-curve" method (Hansen, 1990) or other methods for any spatial distribution (or pattern) of body surface potentials $\Phi$ or magnetic field B, provided a pre-designed weighting matrix W. Subsequently, the regularization parameter can be mathematically expressed as a function of $\Phi$ (or B) and W.

To image the 3-D cardiac electrophysiological process, the source estimate $\hat{J}(t)$ may be desired for all the time points. Regularization schemes can be applied, including: 1) choose $\lambda$ for distinct time points separately, and 2) choose $\lambda$ for time points simultaneously. The former involves solving the inverse problem from body surface electrical potentials instant by instant, as Eq. (19):

$$\hat{J}(t)=H(\lambda_t)\Phi_b(t), \text{ where } \lambda_t=\lambda(\Phi_b(t),W) \qquad (19)$$

The second scheme is based on singular value decomposition (SVD) of the spatiotemporal matrix of body surface electrical potentials $\Phi_b=[\Phi_b(1),\Phi_b(2),\ldots,\Phi_b(T)]$, written as Eq. (20):

$$\Phi_b = U\Sigma V^T = \sum_{k=1}^{\min(T,M)} u_k \sigma_k v_k^T \qquad (20)$$

where $\{u_k\}$ represents a group of spatial components of body surface electrical potentials and $\{v_k\}$ represents their corresponding time courses. The spatial components that do not satisfy the discrete Picard condition (Hansen, 1990) may not be sufficiently smooth to be associated with any source configurations and may be dominated by noise perturbation. In some implementations, these components may be truncated. The spatial distribution of the sources that account for each of the P remained spatial components can be obtained by Eq. (21):

$$\hat{J}_k=H(\lambda_k)u_k, \text{ where } \lambda_k=\lambda(u_k,W) \qquad (21)$$

Multiplied by their corresponding time components $\{v_k|k\leq P\}$ and weighted by the singular values $\{\sigma_k|k\leq P\}$, the entire spatiotemporal current source distribution $\hat{J}=[\hat{J}(1),\hat{J}(2),\ldots,\hat{J}(T)]$ can be reconstructed, as Eq. (22)

$$\hat{J} = \sum_{k=1}^{P} \hat{J}_k \sigma_k v_k \qquad (22)$$

When the equivalent current density inverse problem has been solved, the cardiac electrophysiological properties for each 3-D grid point, such as activation time, repolarization, action potential duration, etc., can be estimated as described in Eqs. (5) and (6).

The algorithms described above can be applied to solving other inverse equations using intra-cavity biosignals or magnetic signals, or hybrid measurements.

Example 2

3-D Cardiac Activation Imaging from Intra-Cavity Potentials Using a Heart Electrophysiological Model Based Imaging Algorithm In some embodiments, the feasibility of imaging 3-D cardiac activation sequences can be illustrated by computer simulations. The inputs can be intra-cavity electrical potentials over a catheter surface, according to some implementations. The algorithms described by eq. (1) and eq. (2) can be used, including using a heart cellular-automaton model to simulate cardiac electrical activity. The activation time throughout the ventricles can be estimated from catheter surface potential maps (CSPMs).

Figure 7A:
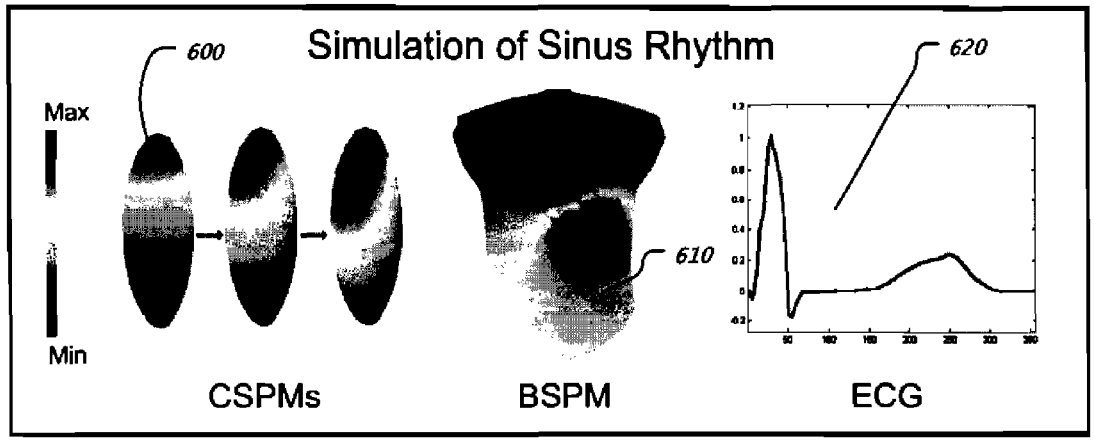
FIG. 7A is an example of the forward solution of the BSPM, cardiac surface potential map (CSPM), chest ECG lead during sinus rhythm.

The forward problem can be solved by means of the finite element method, according to an implementation. FIG. 7A shows the simulated the CSPM 600 over a balloon catheter, body surface potential map (BSPM) 610, and lead-2 ECG 620 during sinus rhythm. In this simulation study, the catheter was placed inside the left ventricular blood cavity.

Figure 7B:
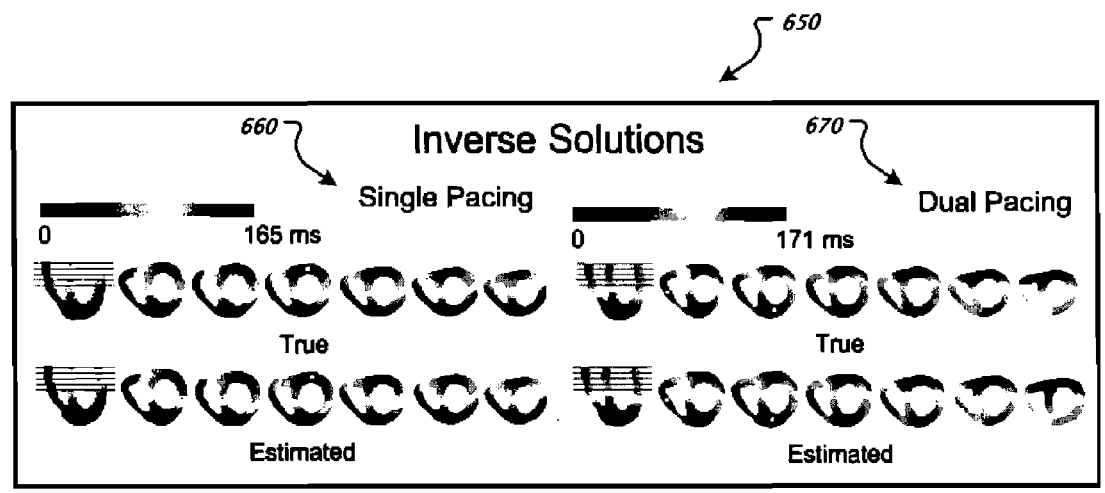
FIG. 7B show examples of the heart electrophysiological model based 3-D activation imaging from intra-cavity potentials. Left panel: single site pacing; Right panel: dual site pacing. Top row: simulated target activation sequence. Bottom row: estimated activation sequence.

A pacing protocol can be used to evaluate the performance of embodiments that perform 3-D cardiac electrical imaging from catheter recordings. In an implementation, twelve sites may be selected and paced individually from the following regions throughout the ventricles: BA: basal-anterior; BRW: basal-right-wall; BP: basal-posterior; BLW: basal-left-wall; BS: basal-septum; MA: middle-anterior; MP: middle-posterior; MLW: middle-left-wall; MS: middle-septum; AA: apical-anterior; and AP: apical-posterior; AS: apical-septum. For each pacing site, assuming the peak-peak value of the catheter surface potential is 5 mV, Gaussian white noise (GWN) of 25-μV can be added to the calculated CSPMs to simulate the noise-contaminated CSPM measurements, which served as the input of the inverse approach. In addition, random noise (e.g., having an average value of 1.2 mm) may also be added to the catheter electrode positions to simulate electrode position uncertainty. A typical example of the present inverse solution 650 during single-site pacing 660 is shown in FIG. 7B (left panel). The CSPMs from $T_1=21$ ms to $T_2=48$ ms after the onset of pacing can be used to inversely estimate the location of the pacing site and the ventricular activation sequence. The localization error (LE) can be assessed by the distance from the localized site of origin of activation to the true pacing site. Estimation error for the activation sequence can be assessed by relative error (RE) between the true and estimated activation sequences. Simulation results for single-site pacing over twelve pacing sites are shown in Table 1. As shown in Table 1, the mean and standard deviation of the LE and RE are 1.88±0.92 mm and 0.03±0.01, respectively, when additive measurement noise is considered. When both additive measurement noise and electrode position uncertainty are considered, the mean and standard deviation of the LE and RE become 2.76±1.22 mm and 0.04±0.02, respectively.

TABLE 1

| Region | 25 μV Noise | | 25 μV Noise + Electrode Uncertainty | |
| --- | --- | --- | --- | --- |
| | LE (mm) | RE | LE (mm) | RE |
| BA | 3.35 | 0.04 | 1.50 | 0.02 |
| BLW | 3.35 | 0.04 | 3.35 | 0.04 |
| BS | 2.12 | 0.03 | 1.50 | 0.01 |
| BRW | 0 | 0 | 5.61 | 0.08 |
| BP | 1.50 | 0.02 | 3.00 | 0.04 |
| MA | 2.60 | 0.04 | 2.12 | 0.03 |
| MP | 2.12 | 0.03 | 3.67 | 0.04 |
| MLW | 1.50 | 0.02 | 2.12 | 0.04 |
| MS | 1.50 | 0.04 | 2.12 | 0.04 |
| AP | 1.50 | 0.03 | 3.67 | 0.05 |
| AS | 1.50 | 0.02 | 1.50 | 0.02 |
| AA | 1.50 | 0.03 | 3.00 | 0.06 |
| Mean | 1.88 ± 0.92 | 0.03 ± 0.01 | 2.76 ± 1.22 | 0.04 ± 0.02 |

TABLE 2

| Trial | 25 μV Noise | | 25 μV Noise + Electrode Uncertainty | |
| --- | --- | --- | --- | --- |
| | LE (mm) | RE | LE (mm) | RE |
| 1 | 1.50 & 3.35 | 0.03 | 2.60 & 6.00 | 0.06 |
| 2 | 3.35 & 1.50 | 0.04 | 3.35 & 1.50 | 0.04 |
| 3 | 1.50 & 4.74 | 0.04 | 2.12 & 3.00 | 0.03 |
| 4 | 3.35 & 1.50 | 0.04 | 3.35 & 1.50 | 0.04 |
| 5 | 2.12 & 2.60 | 0.04 | 2.12 & 2 60 | 0.04 |
| 6 | 3.35 & 4.50 | 0.05 | 5.41 & 7.79 | 0.09 |
| 7 | 4.50 & 3.35 | 0.06 | 2.60 & 3.35 | 0.06 |
| 8 | 3.00 & 2.12 | 0.04 | 6.87 & 2.60 | 0 08 |
| 9 | 1.50 & 3.35 | 0.04 | 1.50 & 3.35 | 0.04 |
| 10 | 3.67 & 1.50 | 0.05 | 2.12 & 2.12 | 0.03 |
| 11 | 0 & 1.50 | 0.01 | 2.12 & 6.18 | 0.08 |
| 12 | 2.12 & 3.35 | 0.06 | 1.50 & 3.35 | 0.06 |
| Mean | 2.64 ± 1.20 | 0.04 ± 0.01 | 3.29 ± 1.81 | 0.05 ± 0.02 |

The performance of the CSPM-based inverse approach may also be evaluated by dual-site pacing. Twelve pairs of myocardial cell units in a seven-layer myocardial region adjacent to the atrial-ventricular (AV) ring may be randomly selected to simulate two localized regions of activation. GWN of 25-μV may be added to the forward-calculated CSPMs. FIG. 7B (right panel) shows an example of inverse solutions during dual-site pacing 670. Table 2 lists the LE and RE for all twelve pairs of pacing sites. As shown in Table 2, on average, the RE of the activation sequence are 0.04±0.01, and the LE over twenty-four initial activation sites is 2.64±1.20 mm, when additive measurement noise is considered. When both additive measurement noise and electrode position uncertainty are considered, the mean and standard deviation of the LE and RE become 3.29±1.81 mm and 0.04±0.02, respectively.

These simulation results may suggest that imaging ventricular activation sequences and localizing sites of ventricular activation during single- or dual-site pacing using the CSPM-based inverse approach is feasible. In some implementations, catheter mapping of intra-cavity potentials at multiple sites simultaneously may enable localizing and imaging of cardiac electrical activity in a 3-D space. The finite element method may be used in this example to solve the forward problem and a cellular-automaton heart-excitation model for simulating ventricular activation. The feasibility of imaging a cardiac activation sequence and localizing the site of initiation of activation has been shown in computer simulations using single-site and dual-site pacing protocols. The small localization errors (on average 2-3 mm localization error for single-site pacing, and 2.6-3.3 mm localization error for dual-site pacing) may suggest potential clinical applications for this approach to accurately localize a ventricular activation site of origin from the widely used catheter procedure in a clinical setting. Using electrical potential recordings on a catheter, 3-D cardiac imaging of electrical activity may be realized. The above example may also be extended to other intra-cavity electrical signals instead of electric potentials.

Example 3

3-D Cardiac Activation Imaging from Body Surface Potentials Using a Heart Biophysical Model Based Imaging Algorithm Cardiac activation sequence throughout the 3-D ventricles can be imaged from body surface potential maps (BSPMs) by means of a heart biophysical model based imaging algorithm. The details of the algorithms are described in equations (7)-(13) and equations (17)-(22). Computer simulations can be conducted to evaluate the performance of embodiments of the method in imaging a cardiac activation sequence in a 3-D heart volume.

Procedures:

Referring to FIG. 5, a piece-wise homogeneous heart-torso model 700, was built from the CT images of a human subject. The numbers of triangles for the body surface, left lung, right lung, heart surface, left blood cavity and right blood cavity were 3280, 1170, 1152, 2676, 454 and 214 respectively. Conductivities of the myocardial tissue, intraventricular blood masses, lungs and the torso were set to 0.2 S/m, 0.67 S/m, 0.05 S/m and 0.21 S/m, respectively. The 3-D ventricular myocardial volume 710 was discretized into 36,709 grid points evenly spaced by 1.5 mm. The forward calculation from a dipole component at any grid point to the electrical potentials at all the electrode locations was numerically implemented by the boundary element method. The locations of various numbers of electrodes (64, 96, 128, 155 and 200) were selected to cover the anterior and posterior chests.

A ventricular excitation process was simulated by a cellular automaton heart model (He et al., 2003). A generalized cardiac anisotropy was incorporated into the heart model. The myocardial fiber orientations rotated counterclockwise over 120° from the outermost layer (epicardium, −60°) to the innermost layer (endocardium, +60°) with identical increment between the consecutive layers. All units on the same myocardial layer of ventricles, ranging from the epicardial layer to the endocardial layer, had identical fiber orientation. The conduction velocity was 0.8 m/s along the fiber and 0.3 m/s transverse to the fiber. The heart model was made up of tens of thousands of myocardial units spaced by 1.5 mm. Each myocardial unit's parameters (e.g., a pattern of action potential, a vector of local fiber orientation, or the like) were set individually. When calculating instantaneous current sources in the cellular automaton model, we considered anisotropy of intracellular conductivities (0.3 S/m along the fiber and 0.075 S/m transverse to the fiber). A conductivity tensor at each cell unit was computed from the local fiber orientation. The three orthogonal components of current source at each cell unit were respectively computed as the product of a negative gradient of instantaneous transmembrane potential at each of three directions and a corresponding intracellular conductivity at the same direction. The time resolution of the cellular automaton heart model is 1 ms.

Two simulation protocols, namely single-site pacing and dual-site pacing, were applied to generate the ventricular excitation process. For the single-site pacing, twelve pacing sites were selected and named according to the ventricular segment that they belonged to based on ventricular anatomic structure. Their abbreviations were described as follows: BA: basal-anterior, BRW: basal-right-wall, BP: basal-posterior, BLW: basal-left-wall, BS: basal-septum, MA: mid-anterior, MRW: mid-right-wall, MP: mid-posterior, MLW: mid-left-wall, MS: mid-septum, AA: apical-anterior, and AP: apical-posterior. For the dual-site pacing, one pacing site was fixed at the mid-lateral RV free wall while the other was varied. The two pacing locations were either paced simultaneously, or the variable pacing site was paced 20 ms after the fixed pacing location.

Gaussian white noise of various noise level (e.g., 0, 5, 10, 20, 40, 60 μV) was added to the calculated body surface signals (peak-to-peak range of around 3 mV), to simulate the ECG measurements. These noise levels correspond to the signal-to-noise ratios of infinity, 41, 35, 29, 23 and 20 dB, respectively, for the simulated ECG measurements during ventricular activation. Effects of geometric errors were also examined by translating the heart position (toward the right lung) within the torso by 5 mm, or/and expanding the volume of the torso by 10%. Referring to FIG. 6, after introducing the geometric errors, the heart-torso volume conductor model 720 was used to simulate the body surface potential measurements 730, while the original model before introducing the geometric errors was used for solving the 3-D activation imaging problem.

Figure 8:
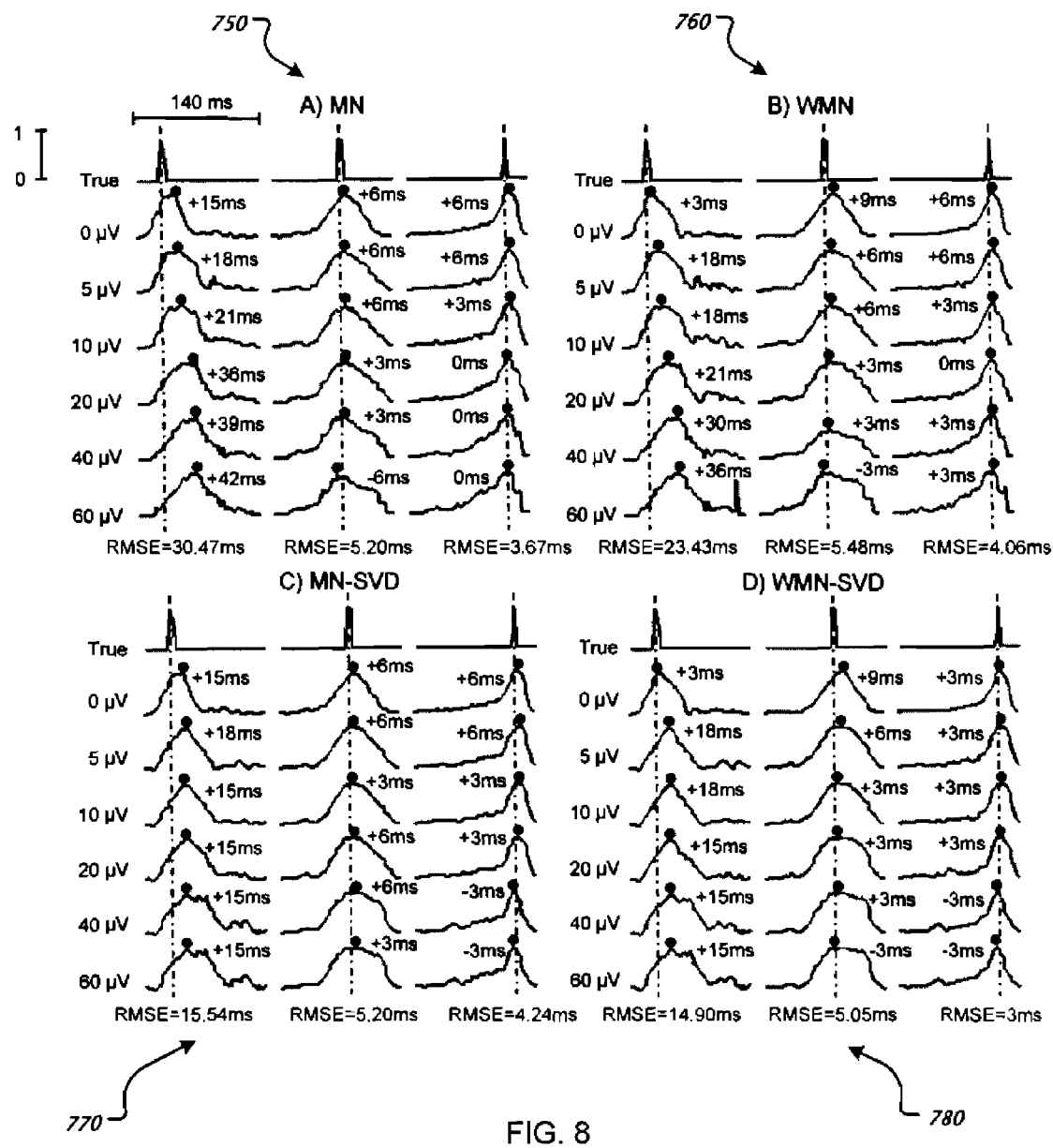
FIG. 8 depicts an exemplary comparison between the normalized time course of estimated current density under different noise levels and the true current density waveforms using four algorithms.

Referring to FIG. 8, to estimate the spatiotemporal distribution of the equivalent current density, four inverse approaches were applied. A minimum norm (MN) 750 and a weighted minimum norm (WMN) 760 used conventional instant-by-instant selection of the regularization parameter. SVD-based regularization was used in the other two approaches, denoted as "MN-SVD" 770 and "WMN-SVD" 780. To quantify the performance of the proposed noninvasive 3-D activation sequence imaging approach, the correlation coefficient (CC) and relative error (RE) were calculated to measure the overall agreement or disagreement between the inversely estimated activation sequence and the "true" activation sequence simulated by the cellular automaton heart model. The capability of localizing the origin(s) of excitation was evaluated by the localization error (LE), which may be defined as the distance from the true pacing location(s) to the center of mass of the locations with the minimal activation time in the estimated activation images, according to some implementations.

Results:

FIGS. 8A-8B show the comparison between the normalized time course of estimated current density under different noise levels and the true current density waveforms. To facilitate the comparison morphologically, absolute values of current density estimates were normalized into [0,1] for every grid point separately. Three locations, whose true activation times were 20 ms, 80 ms and 120 ms, respectively, were selected as representative myocardial sites activated during the early, middle or late stage of ventricular depolarization. For the locations of middle and late activation, the "peaks" of the estimated current density arrived at about the same time as those of the simulated current density, with their difference in time as small as 3~6 ms, on average. This estimation error did not further deteriorate with increasing noise levels (up to 60 μV). In contrast, a considerable delay of the estimated activation time was observed at the early activated location. Even at zero noise level, such a delay was as large as 15 ms for the MN solution. At higher noise levels, the estimation error of using the instant-by-instant regularization became increasingly large (as shown in FIGS. 8A-8B), thereby reducing the imaging contrast between the locations of early and middle activation. On the other hand, using the SVD-based regularization, such a deteriorative error can be confined to a relatively constant level (around 15 ms). The results in FIGS. 8A-8B suggest using the SVD-based regularization causes smaller errors in the estimation of the early activation times, compared to the conventional instant-by-instant regularization.

The variation of imaging accuracy in response to different locations of the ventricular excitation origin was further tested over twelve pacing sites respectively located at different ventricular segments as aforementioned. Simulation results based on 200-channel BSPM under 20 μV noise level are summarized in Table 3. As shown in Table 3, for each of the twelve cases, SVD-based regularization gave rise to improved performance over the instant-by-instant regularization in terms of CC and RE. In addition, the SVD-based regularization resulted in much smaller means and standard deviations in terms of LE than the instant-by-instant regularization did, and WMN-SVD was slightly better than MN-SVD. From Table 3, it may be seen that the imaging result was more accurate when the activation was initiated from the LV or RV free walls than from the septum. Similarly, the imaging performance was better when paced at the anterior than at the posterior.

TABLE 3

| Origin | MN | | | MN-SVD | | | WMN | | | WMN-SVD | | |
|---|---|---|---|---|---|---|---|---|---|---|---|---|
| | CC | RE | LE | CC | RE | LE | CC | RE | LE | CC | RE | LE |
| BRW | 0.89 | 0.17 | 4.97 | 0.91 | 0.16 | 4.24 | 0.87 | 0.17 | 1.50 | 0.93 | 0.14 | 3.67 |
| BLW | 0.93 | 0.17 | 2.60 | 0.94 | 0.15 | 3.35 | 0.94 | 0.16 | 24.19 | 0.95 | 0.14 | 6.87 |
| BP | 0.91 | 0.23 | 7.65 | 0.92 | 0.21 | 8.62 | 0.85 | 0.27 | 9.60 | 0.88 | 0.25 | 7.79 |
| BA | 0.93 | 0.18 | 23.76 | 0.94 | 0.17 | 11.72 | 0.90 | 0.23 | 22.35 | 0.91 | 0.23 | 6.87 |
| BS | 0.93 | 0.15 | 3.67 | 0.94 | 0.14 | 5.41 | 0.94 | 0.12 | 5.61 | 0.95 | 0.11 | 4.50 |
| MRW | 0.87 | 0.20 | 5.61 | 0.91 | 0.16 | 11.23 | 0.85 | 0.19 | 7.65 | 0.90 | 0.15 | 4.97 |
| MLW | 0.87 | 0.20 | 19.21 | 0.92 | 0.17 | 8.08 | 0.88 | 0.20 | 13.91 | 0.92 | 0.18 | 4.50 |
| MP | 0.88 | 0.24 | 16.77 | 0.90 | 0.22 | 3.35 | 0.82 | 0.30 | 15.66 | 0.82 | 0.29 | 3.67 |
| MA | 0.90 | 0.18 | 2.12 | 0.90 | 0.17 | 4.50 | 0.91 | 0.15 | 3.00 | 0.92 | 0.14 | 3.35 |
| MS | 0.83 | 0.30 | 5.61 | 0.83 | 0.29 | 6.18 | 0.75 | 0.35 | 3.67 | 0.77 | 0.34 | 8.62 |
| AP | 0.95 | 0.16 | 17.36 | 0.95 | 0.15 | 6.87 | 0.95 | 0.16 | 17.36 | 0.96 | 0.15 | 4.50 |
| AA | 0.94 | 0.16 | 14.15 | 0.95 | 0.15 | 6.18 | 0.94 | 0.17 | 14.15 | 0.95 | 0.16 | 6.54 |
| Mean | 0.90 | 0.19 | 10.29 | 0.92 | 0.18 | 6.64 | 0.88 | 0.20 | 11.56 | 0.90 | 0.19 | 5.49 |
| STD | 0.04 | 0.04 | 7.49 | 0.03 | 0.04 | 2.81 | 0.06 | 0.07 | 7.57 | 0.06 | 0.07 | 1.77 |

Figure 9:
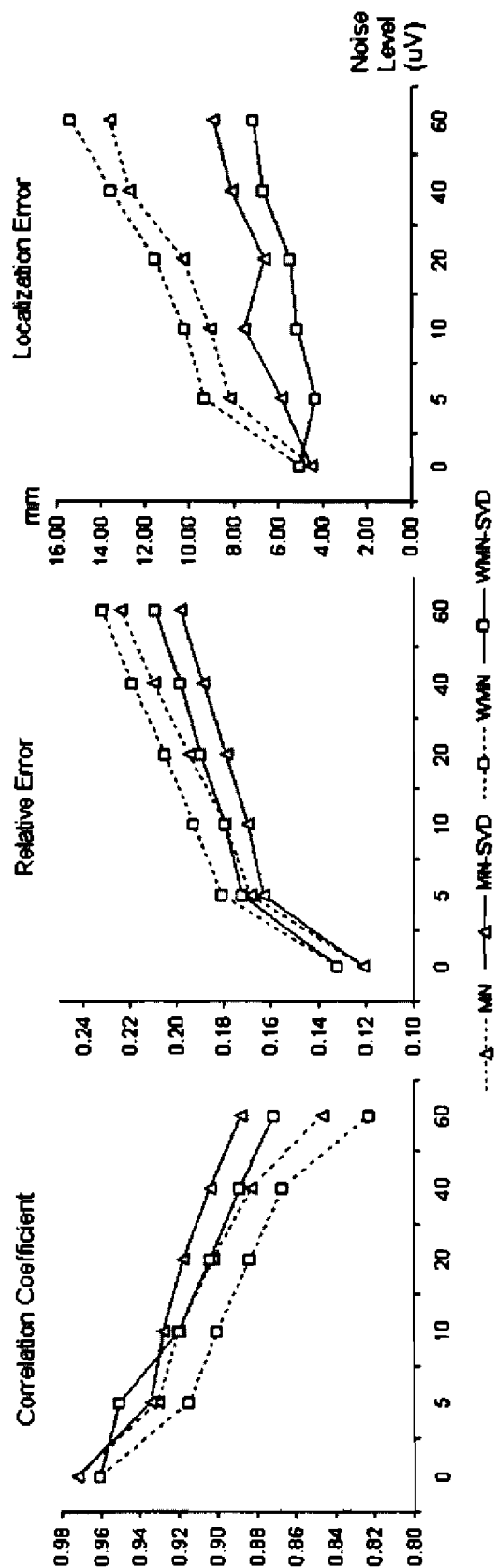
FIG. 9 depicts exemplary effects of measurement noise on the performance of different inverse imaging algorithms for the heart biophysical model based 3-D cardiac activation imaging from BSPMs.

FIG. 9 depicts the effect of measurement noise on the performance of different inverse algorithms. Under each of six noise levels (0, 5, 10, 20, 40 and 60 µV), the values of the three evaluation variables were averaged over all twelve cases of pacing sites when 200 electrodes were used. The linear inverse approaches based on the SVD-based regularization had better performance than the instant-by-instant regularized methods, in terms of all three of the evaluation variables (CC, RE and LE), and especially for LE. The SVD-based regularization tended to perform increasingly better than the instant-by-instant regularization as higher levels of noise were present. In terms of CC and RE, MN-SVD was better than WMN-SVD, but WMN-SVD had smaller localization error than MN-SVD. These results demonstrate that even with the noise level as high as 60 µV, the 3-D activation sequence imaging technique described herein can reconstruct on average over 87% of the true activation sequence with the relative error at around 0.20 and the error of localizing the origin of activation less than 7 mm on average, according to an implementation.

Figure 10:
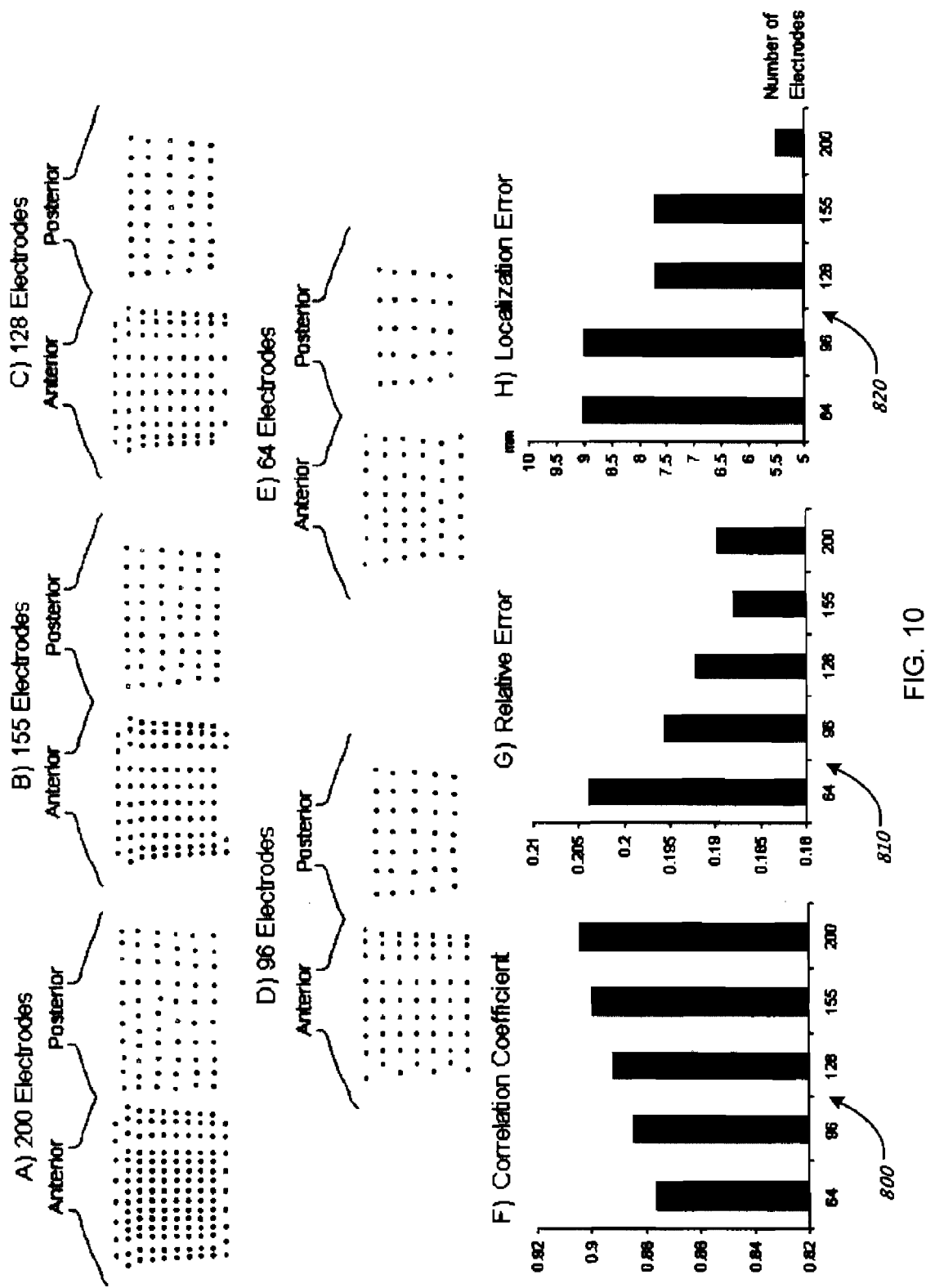
FIG. 10 depicts exemplary effects of the number of electrodes on the imaging results.

The effect of the number of electrodes on the imaging results were considered. Using WMN-SVD, the 3-D activation imaging was performed for twelve single-site paced beats under 20 µV noise level. Five different configurations (with 200, 155, 128, 96 and 64 electrodes respectively), were selected from the anterior and posterior chests as shown in FIG. 10[A, B, C, D, E]. Using the same number of electrodes, the CC, RE and LE were averaged over twelve different pacing locations. FIG. 10 [F, G, H] shows the averaged CC, RE, LE as a function of the number of electrodes. As shown in FIG. 10, higher density of electrodes resulted in better imaging accuracy and smaller localization error. However, using sixty-four electrodes, a high CC of 0.8764 (800), low RE of 0.204 (810) and small LE of 9 mm (820) could be achieved.

Figure 11:
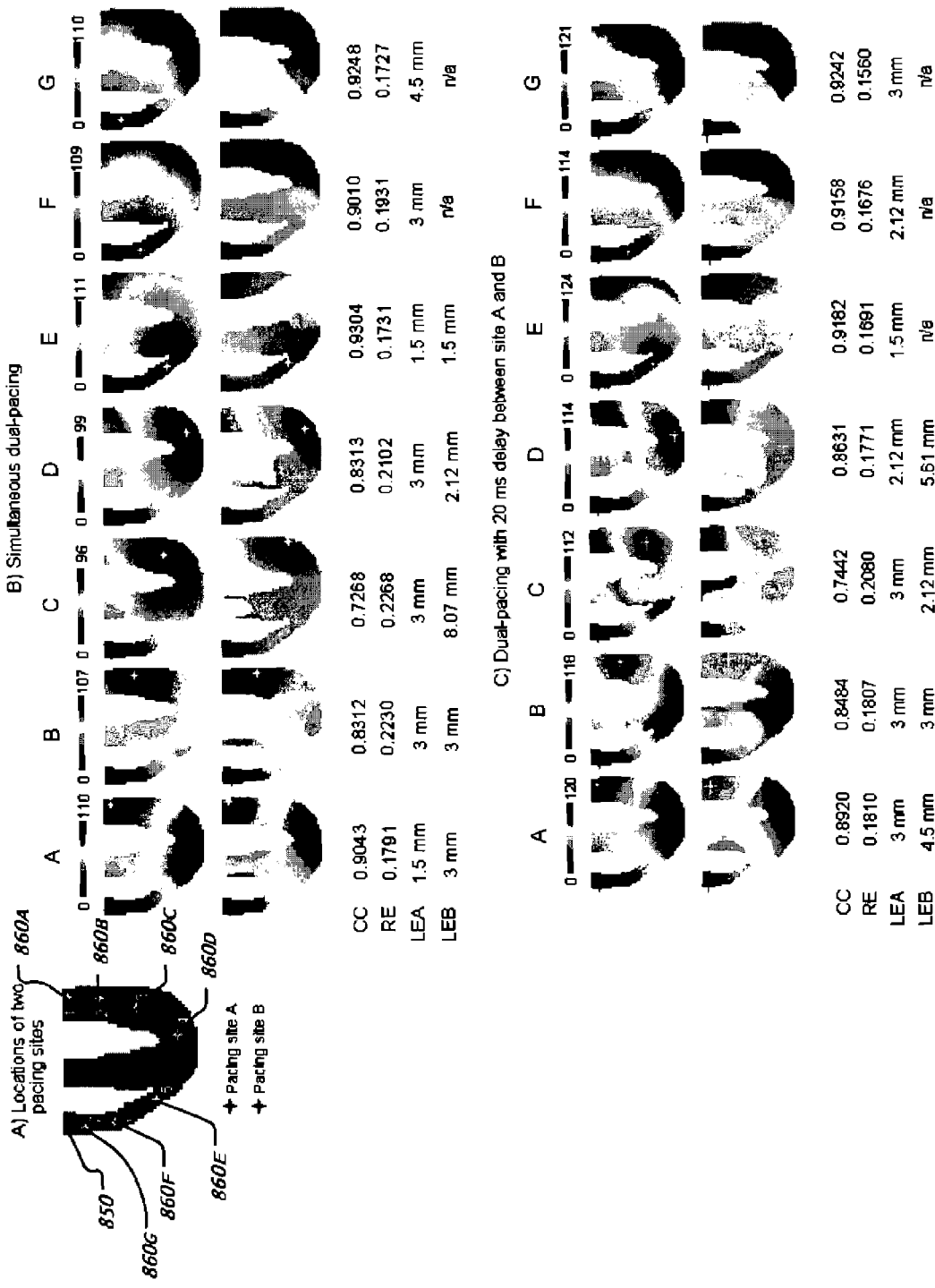
FIG. 11 depicts examples of three-dimensional activation imaging for two wavefronts initiated from two simultaneously paced sites.

The 3-D activation sequence initiated from two simultaneously paced sites was imaged to assess the imaging accuracy and capability of localizing two pacing sites. Two pacing locations (a stationary site 850 and a variable site 860 stars) are shown in FIG. 11A. The Stationary site 750 was fixed at the basal-lateral RV free wall, while the variable site 860 consisted of seven different locations labeled A-G (860A-860G, respectively). The activation sequence for each of the seven paced beats was imaged using WMN-SVD from 200-channel BSPM under 20 µV noise level. The imaging results were compared with the simulated true activation sequence, as shown in FIG. 11B. From the imaged activation sequence, the dual-site paced activation pattern may be reconstructed with high CC and low RE. The two pacing sites may be resolved for five out of the seven cases when the inter-site distance was larger than 4-5 cm (cases A through E), except when the distance between two pacing sites were less than 2.1 cm in the lateral RV free wall. Extended areas of earliest activation time were found around the two pacing locations, and the centers of these regions were close to the true pacing sites with the largest LE of 8.07 mm for site B, as shown in FIG. 11B. When the two pacing sites were close to each other, as in cases F and G for example, they appeared as a single pacing site. This result may further demonstrate that the imaging method has a low spatial resolution of localizing the origin of activation.

Cases of dual-pacing with 20 ms delay (the variable site 860 was paced 20 ms after the stationary site 850 was paced) were also tested. The pacing locations were the same as shown in FIG. 11A. FIG. 11C shows the imaging results in comparison with the simulated true activation sequence. Similar to the results for simultaneous dual-pacing, the overall pattern of activation propagation was reconstructed with reasonable accuracy. The two pacing sites were resolvable for four out of the seven cases. In cases A through D, we found from the imaged activation sequence that the region surrounding variable site 860 was activated later than the region around stationary site 850 with a time delay ranging from 16 ms to 27 ms, which was close to the "true" delay of pacing (i.e. 20 ms) between these two pacing sites. In cases E and F, two pacing sites could not be resolved in the imaged activation sequence, appearing as if there was one pacing location, although in the true activation sequence it was observable that the variable site 860 was activated before its surrounding area. In case G, variable site 860 was paced after it was activated as the excitation wavefront propagated from the stationary site 850 to the variable site 860. This dual-pacing case may be effectively equivalent to single-pacing from the stationary site 850 alone. This imaged activation sequence also revealed a single pacing site with a LE of 3 mm.

Discussion:

Imaging the 3-D ventricular activation sequence by means of modeling and imaging the equivalent current density throughout the ventricular myocardium has been shown in the example described above. Computer simulations to evaluate the approach using single-site and dual-site pacing protocols have been conducted. The simulation results suggest that the single-site paced activation sequence can be accurately reconstructed using 200 body-surface electrodes with a high overall accuracy. For example, under 20 µV noise level, the average (over twelve pacing sites throughout the ventricles) CC and RE were 0.90 and 0.19, and the origin of the activation could be localized with the average LE of 5-6 mm. The SVD-based regularization scheme had improved performance over the conventional instant-by-instant regularization scheme, showing higher CC, and lower RE and LE for most of the cases in the simulation. For the SVD-based regularization, the noise had less effect on the imaging results. Even under a high level of noise (e.g. 60 µV), acceptable reconstruction accuracy could still be achieved with the averaged CC larger than 0.87 and the averaged RE around 0.20, and the localization error could be confined to be around 7-8 mm on average. The performance by use of the instant-by-instant regularization was more sensitive to the measurement noise. The simulation results on the effect of the number of electrodes may demonstrate that even with 64 channels on body surface it may still be feasible to achieve a reasonable imaging accuracy and localization capability, but a higher density electrode array can further improve the performance. The simulation results on the effect of volume conductor modeling errors may demonstrate that the proposed imaging algorithm has reasonable robustness against torso geometry uncertainty and heart position uncertainty, although these modeling uncertainties result in additional reconstruction error. Simulations on the capability of resolving and localizing two pacing sites also had promising results. When two sites were paced simultaneously, the two origins of activation could be resolved when they were located at the contralateral sides of ventricles, or even when both were located at the lateral wall of the same ventricle (e.g. the RV in our simulation) given the inter-site distance larger than 4-5 cm. When two pacing sites were paced with a time delay of 20 ms, the 3-D activation sequence was also imaged with a reasonable accuracy. The two origins of activation could be resolved when the two pacing sites were located at RV and apex or contralateral sides of ventricles. A time delay close to 20 ms could be observed between these two origins.

Using techniques disclosed herein, values of activation time exclusively from the time course of current density estimates at each spatial location separately may be extracted. By shifting the view of inspecting the ECG inverse solution from spatial domain to spatio-temporal domains, a physiologically reasonable activation sequence reconstruction may be obtained, even if a large number of dipole sources are estimated.

The shape of the time courses of estimated current density were much less "steep" than the shape of "delta functions" that appeared in the simulated "true" current density waveforms. At each time point of imaging, the regularized linear inverse operators may result in a smooth spatial distribution of the instantaneously reconstructed current density, unlike the narrow-width moving wavefront during the actual excitation process. At different time instants within a short time window, the spatial distribution of the current source estimate may overlap with each other due to the smoothness in space at each time point respectively. Consequently, the current density at any spatial location within the overlapped region may appear as having a much smoother version of the time course than the true current density, as shown in FIG. 8.

Since the discussed techniques of imaging the 3-D activation time are based on an estimation of spatiotemporal current density distribution, a spatiotemporal regularization scheme may be used, rather than separately for each time instant. In this fashion, time-variation of the regularization parameter may have a reduced effect on the inverse solution. Truncating those spatial components that do not satisfy the discrete Picard condition, may "filter" noise components. Also, the regularization parameter may be determined for each spatial component and may remain stable throughout the period of interest. FIG. 8 also shows an example on the efficacy of SVD-based regularization. The linear inverse operator may result in smoothness in both the spatial and temporal distribution of current density estimates in a highly ill-posed condition. A spurious and sharp spike in the estimated current density (as shown in the last row of FIG. 8B) may be unlikely to be associated with source activity, but may be an artifact generated by large recording noise or mis-selection of regularization parameter. As shown in FIG. 8D, the application of SVD-based regularization may remove such an artifact.

Although the minimum norm and weighted minimum norm were applied in the simulation, the 3-D activation imaging techniques are not limited to these two inverse approaches. Many other linear or non-linear inverse algorithms can also be incorporated into solving the 3-D activation imaging problem. For example, different variations of weighted minimum norm, such as Laplacian weighted minimum norm, can be modified from L-2 norm formulations by changing the order of norm to values other than 2 (e.g., between 1 and 2).

Inherent spatio-temporal coherence of cardiac electrical activity and derivation of activation time from 3-D equivalent current density estimation may be used. In some implementations, the entire period of ventricular depolarization may be utilized. To account for an accurate volume conductor modeling, a finite element method (FEM) may be used. Diffusion tensor imaging (DTI) may be used to obtain the information of anisotropic conductivity, in some implementations.

In some examples, the activation time may be estimated from the equivalent current density distribution according to Eq. (5). As shown in FIG. 4B, the repolarization time 490 can also be estimated from Eq. (6), and action potential duration 510 can be estimated as the difference between the activation time 480 and repolarization time 490, for each grid in the 3-D myocardium. Furthermore, the repolarization dispersion may be further imaged by estimating relevant parameters from the repolarization process.

Figure 12:
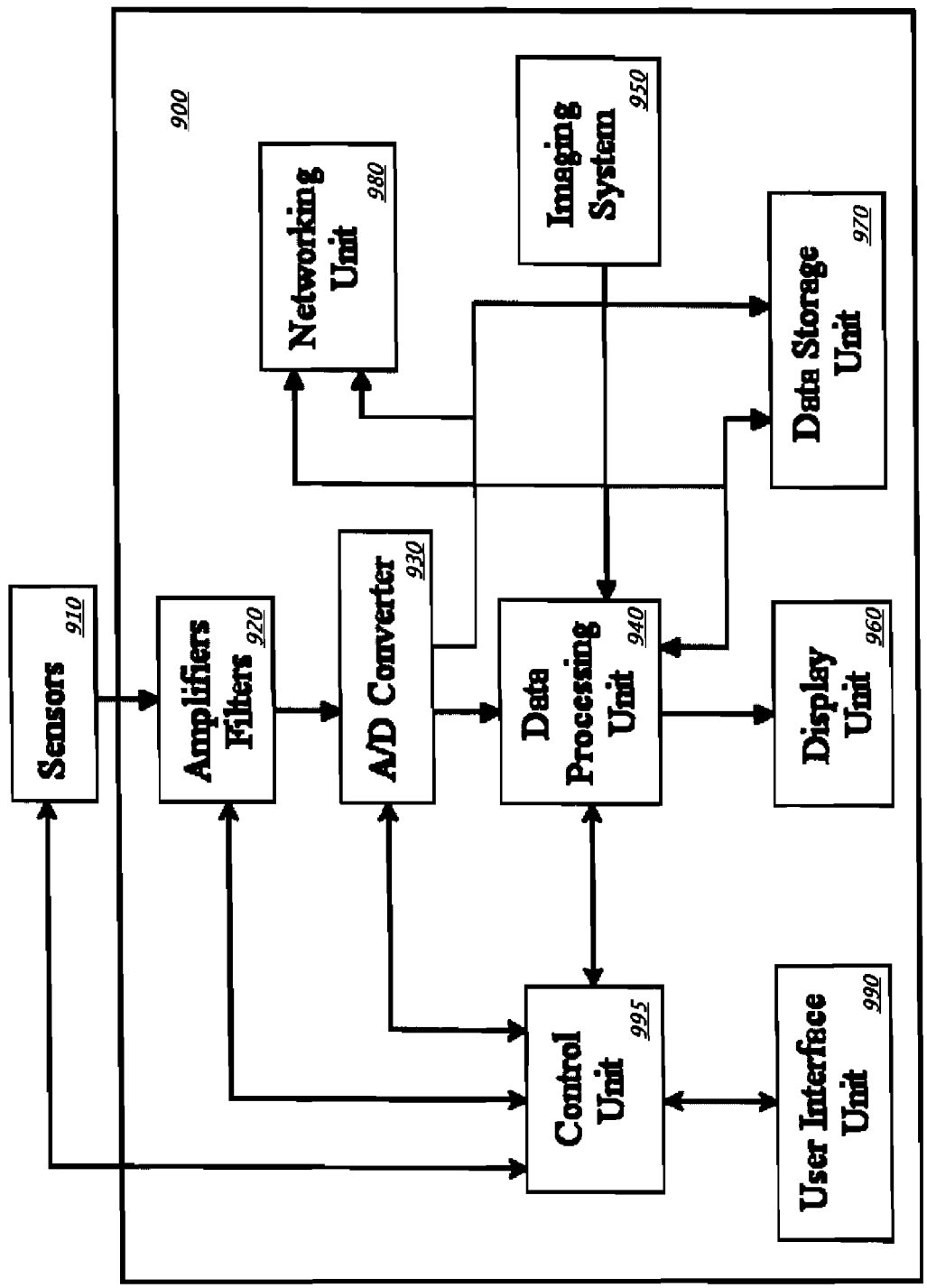
FIG. 12 is an exemplary block diagram of an apparatus that may be used to implement techniques disclosed herein.

Referring to FIG. 12, in some embodiments, an apparatus 900 receives analog signals from sensors 910, which can be incorporated into a catheter for sensing intra-cavity biosignals, which may be attached to the body surface for sensing body surface electrical signals and/or incorporated into a magnetic recording system for sensing magnetic signals. The number of sensors can vary from just a few to several hundred or even thousands. The locations of the recording sensors can be determined by geometry sensors which can be an integrated part of the sensors 910, or different geometry sensors to determine the locations of recording electromagnetic sensors. For example, a near field, low-frequency magnetic field can be generated from a magnetic transmitter and detected with a receiver. The transmitter may contain electromagnetic coils that may emit the magnetic fields. The transmitter can serve as the system's reference frame for receiver measurements. The receiver may contain electromagnetic coils that detect the magnetic fields emitted by the transmitter. The sensed signals can be used to compute the receiver's position and orientation relative to the transmitter.

In this exemplary embodiment, the sensed analog signals (electrical or magnetic) are processed with amplifiers and filters 920 following a methodology known to an individual skilled in the art. After processing, the signals may be converted to digital form by an A/D converter 930. The digitized data may then be sent to a data processing unit 940. Additional data sent to the data processing unit 940 may include data such as geometry information of the subject's torso and heart by means of an imaging system 950 (e.g., magnetic resonance imaging, computer tomography, ultrasound imaging, fluorescent imaging, or the like). These electromagnetic signals, together with sensor location information and the geometry information of the subject's torso and heart, may be processed in the data processing unit 940 using the cardiac electrophysiological imaging methods to estimate the spatial or spatio-temporal distribution of cardiac electrical activity, including, for example, cardiac activation time, repolarization time, action potential duration, transmembrane potential, intracellular potential, extracellular potential, and other derived quantities representing electrophysiological properties of the regional myocardial tissue. The imaging results can be displayed on a display unit 960 (e.g., on a monitor or printer), either alone or coregistered to other anatomical imaging results such as fluorescent images, ultrasound images, magnetic resonance images, or computer tomographic images, with imaging inputs from the imaging system 950 and processed for coregistration at the data processing unit 940. The results, as well as the digitized original data, can be sent to a storage unit 970 and/or to additional locations through a networking unit 980. Included in the apparatus 990 can be a user interface unit 990 and a control unit 995. The user interface unit 990 can allow an operator to interact with the apparatus 900. The control unit 995 can synchronize the operation of the apparatus 900 in conjunction with other systems (e.g., guide a catheter ablation procedure). In some embodiments, the imaging of 3-D cardiac electrical activity, including cardiac activation and repolarization properties and their derived quantities, may be carried out in the data processing unit 940 using the cardiac electrophysiological imaging techniques, which are described in detail above. The components or modules shown in FIG. 12 may be combined or separated in various manners, and in some implementations, various components may be omitted. The initial processing, including filtering, amplification and A/D conversion may also be performed at the locations of sensors, and such processed signals may be transmitted by wire or wirelessly to the data processing unit 940. Functionality may be implemented in hardware or software as desired, depending upon the implementation.

Figure 13:
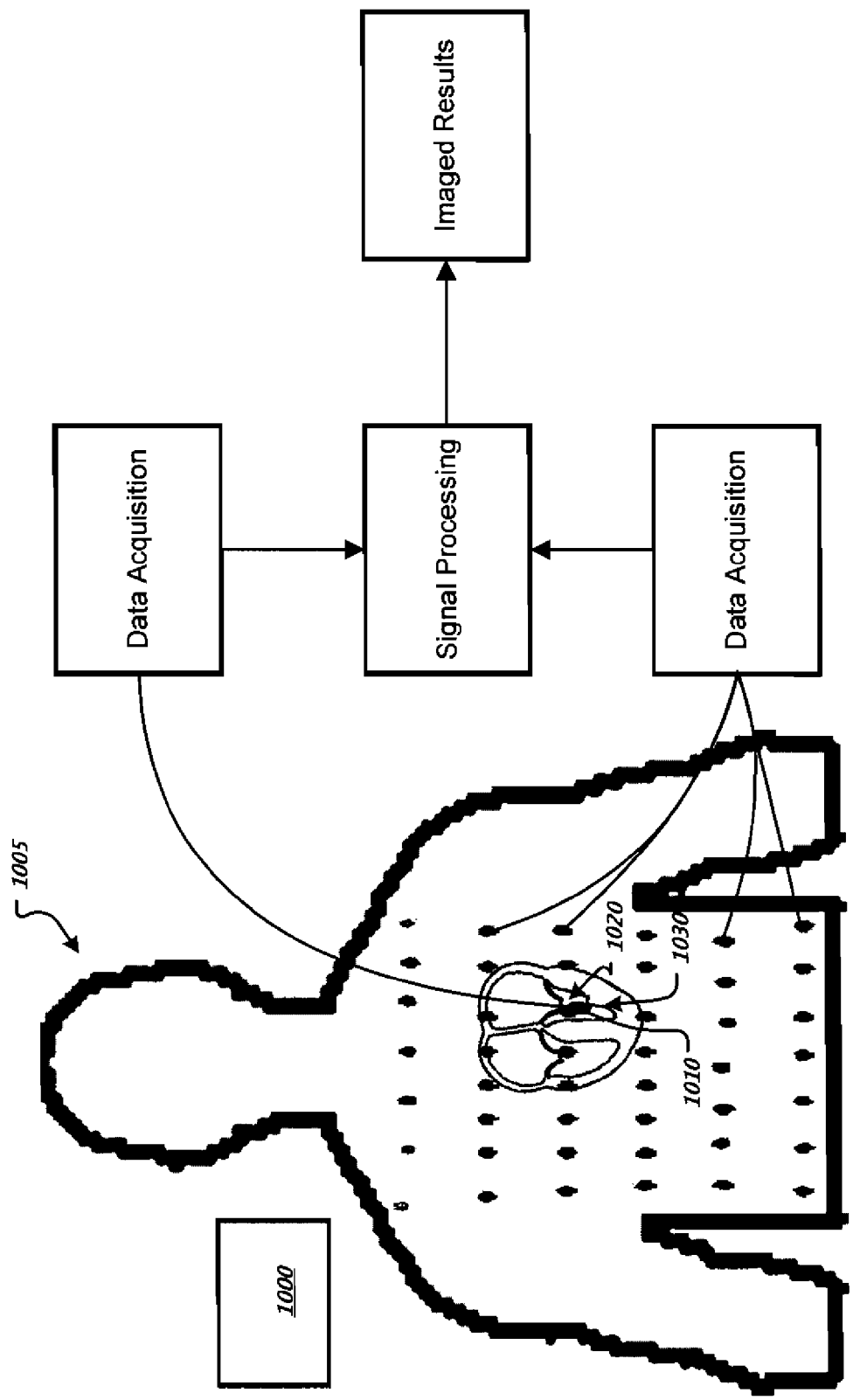
FIG. 13 is a block diagram of an apparatus of one embodiment of the invention, using the intra-cavity biosignal recordings, and/or body surface biosignal recordings.

Referring to FIG. 13, in some embodiments, a transmitter 1000 that contains electromagnetic coils that can be used to emit magnetic fields may be placed outside of a patient 1005 as a reference. A receiver 1010 that contains electromagnetic coils for detecting the magnetic fields emitted by the transmitter 1000 may be combined with a catheter (e.g., on the distil end) and placed into a cardiac cavity 1020 of the patient 1005. The receiver's position and orientation relative to the transmitter 1000 may be computed based on the sensed electromagnetic signals. Multiple transmitters may be used to accurately determine the location of the receiver. Multiple receivers may also be used to determine the locations of the receivers in order to determine the locations of the sensors. By moving the receiver 1010 in the cavity 1020, the geometry and position of the endocardium 1030 may be detected. The position of the catheter 1010 can also be recorded in the same coordinates. The geometry of the endocardium can also be constructed from CT/MRI/ultrasound images in a heart-torso model. A surface-matching technique can be used on the endocardial surfaces to coregister the two sets of coordinates.

Figure 14:
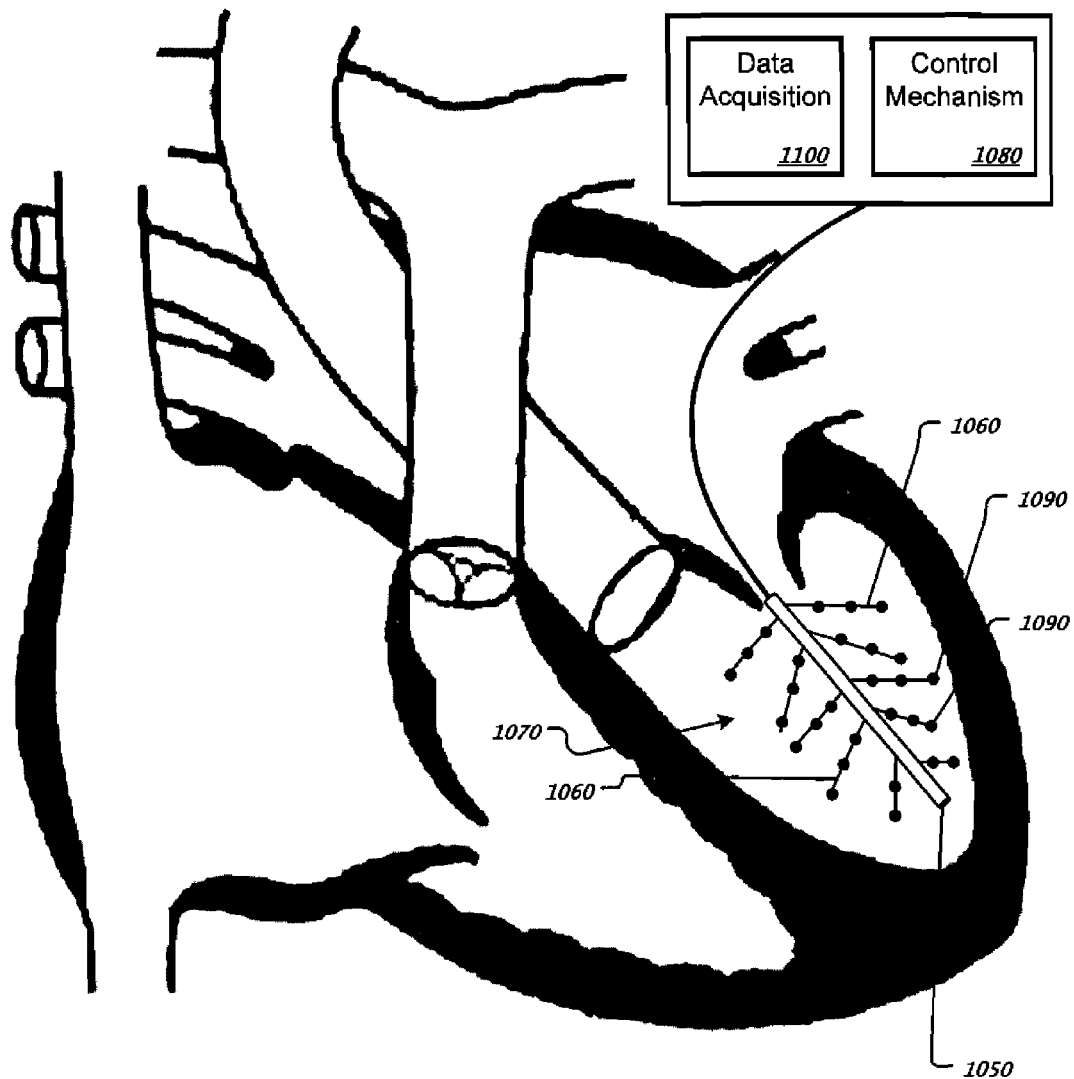
FIG. 14 is an exemplary catheter system with multiple electrode sensor leads that cover a three-dimensional volume within a heart chamber.

Referring to FIG. 14, in some embodiments, a catheter 1050 that includes multiple sensor leads 1060 may be placed within the cavity 1070 of a heart chamber. A control mechanism 1080 may be used to enable the multiple sensors leads be erected within the blood cavity covering a 3-D volume about the catheter 1050. Electrical recordings may be made from the multiple sensors of the leads being erected. Such sensors may also include receivers from which locations of the recording sensors may be determined in the 3-D geometry. Such 3-D electrical and geometry recordings may be used to determine and image cardiac electrical activity within the 3-D myocardial volume.

In some implementations, the sensor leads 1060 may initially be substantially flush against the catheter 1050 so that the catheter may more easily be guided to an intra-cavity location within a heart chamber. The sensor leads 1060 may then be deployed or erected, as by control mechanism 1080, to cover a three-dimensional volume within the heart chamber, as shown in FIG. 14. If the catheter 1050 is to later be moved, the sensor leads 1060 may be controlled to again be positioned substantially flush with the catheter. This may permit convenient routing of the catheter through cardiac arteries or veins, for example.

A number of embodiments have been described. Nevertheless, it will be understood that various modifications may be made without departing from the spirit and scope of the invention. Accordingly, other embodiments are within the scope of the following claims.

What is claimed is:

1. A method of generating a three-dimensional representation of cardiac electrical activity for a subject, the method comprising:

providing a three-dimensional cardiac model comprising a structure of a heart and finite elements on which cardiac electrophysiological properties are considered;

recording, from a catheter having a distal portion comprising multiple electrodes, sensed intra-cardiac electrical potential data for electrical activity sensed by the multiple electrodes while the catheter distal portion is positioned within one or more chambers of the subject's heart;

using the recorded intra-cardiac electrical potential data to estimate a value for an electrophysiological property for each of various finite elements throughout the three-dimensional cardiac model; and generating on a visual display device, and using the calculated values for the electrophysiological property for the various finite elements, a visual representation of estimated cardiac electrical activity for the subject.

2. The method of claim 1, wherein the electrophysiological property is a source model that predicts cardiac electrical activity, and estimates the calculated values for the electrophysiological property by minimizing a difference between the catheter recorded intra-cardiac electrical potential data and the source model predicted cardiac electrical activity.

3. The method of claim 2, wherein the source model is a heart biophysical model comprising three-dimensional equivalent source representations, including one or more of current density, transmembrane potential, local field potential, activation time, and repolarization time.

4. The method of claim 3, wherein the three-dimensional equivalent source representations include estimated equivalent current density representations, and wherein the method further comprises deriving a repolarization dispersion from the estimated equivalent current density representations to aid in diagnosis and management of cardiovascular diseases.

5. The method of claim 1, wherein the estimated cardiac electrical activity comprises cardiac activation.

6. The method of claim 1, wherein the estimated cardiac electrical activity comprises cardiac repolarization.

7. The method of claim 1, wherein the generated visual representation of the estimated cardiac electrical activity is used to guide ablation of cardiac arrhythmias.

8. The method of claim 1, wherein the generated visual representation of the estimated cardiac electrical activity is used to guide catheter ablation of cardiac arrhythmias.

9. The method of claim 1, wherein the generated visual representation of the estimated cardiac electrical activity is used to guide cardiac synchronized therapy.

10. The method of claim 1, wherein the visual representation of the estimated cardiac electrical activity includes representations of cardiac electrical activity both within the three-dimensional volume of the heart and over a surface of the heart.

11. The method of claim 1, wherein the electrophysiological property is an activation time during a cardiac cycle.

12. The method of claim 11, wherein the activation time is a time at which an excitation wavefront would initially appear at the corresponding finite element of the three-dimensional cardiac model.

13. The method of claim 11, wherein the activation time is a time at which current density would reach a maximum at the corresponding finite element of the three-dimensional cardiac model.

14. The method of claim 1, wherein the three-dimensional cardiac model comprises a structural image provided by imaging the heart of the subject from whom the cardiac electrical activity data are collected.

15. The method of claim 1, wherein the catheter comprises electrodes that are located on deployable arms that when deployed extend away from a central body portion of the catheter distal portion such that the electrodes are positionable from the central body portion, occupying a three-dimensional volume within the intra-cavity.

16. The method of claim 1, wherein the catheter comprises electrodes that are configured on the catheter distal portion so that when the catheter distal portion is positioned within a cardiac chamber, each of the electrodes is exposed on substantially all of its sides.

17. A system for generating a three-dimensional representation of cardiac electrical activity for a subject, the system comprising:
a three-dimensional cardiac model comprising a structure of a heart and finite elements on which cardiac electrophysiological properties are considered;
a catheter having a distal portion comprising multiple electrodes adapted to record intra-cardiac electrical potential data for intra-cardiac electrical activity sensed by the multiple electrodes while the catheter distal portion is positioned within one or more chambers of the subject's heart;
an amplifying and processing unit that amplifies and filters the sensed intra-cardiac electrical potential data by the catheter;
a computation unit adapted to process the recorded intra-cardiac electrical potential data to calculate a value for an electrophysiological property for each of various finite elements throughout the three-dimensional cardiac model; and
a displaying unit adapted to generate and display, using the calculated values for the electrophysiological property for the various finite elements, a visual representation of estimated cardiac electrical activity for the subject.

18. The system of claim 17, wherein the computation unit performs computations to estimate the calculated values for the electrophysiological property by minimizing the difference between the recorded intra-cardiac electrical potential data and a heart source model predicted electrical activity data at the same locations of the electrodes of the catheter.

19. The system of claim 17, wherein the visual representation of the estimated cardiac electrical activity for the subject is used to guide ablation of cardiac arrhythmias.

20. The system of claim 17, wherein the visual representation of the estimated cardiac electrical activity for the subject is used to guide catheter ablation of cardiac arrhythmias.

21. The system of claim 17, wherein the visual representation of the estimated electrical activity for the subject is used to guide cardiac synchronized therapy.

22. A method of generating a three-dimensional representation of cardiac electrical activity for a subject, the method comprising:
providing a three-dimensional cardiac model comprising a structure of a heart and finite elements on which cardiac electrophysiological properties are considered;
collecting, from a catheter having a distal portion comprising multiple electrodes, data for electrical activity sensed by the multiple electrodes while the catheter distal portion while is positioned within one or more chambers of the subject's heart;
collecting, from an electrode array positioned on the subject's body surface, data for electrical activity sensed by the body surface electrode array taken during a time period during which the electrical activity data recorded by the catheter are sensed; and
using both the electrical activity data collected using the catheter and the electrical activity data collected using the body surface electrode array to calculate a value for an electrophysiological property for each of the various finite elements throughout the three-dimensional cardiac model; and
generating on a visual display device, and using the calculated values for the electrophysiological property for the various finite elements, a visual representation of estimated cardiac activity data for the subject.

23. The method of claim 22, wherein the estimated cardiac electrical activity comprises cardiac activation.

24. The method of claim 22, wherein the estimated cardiac electrical activity comprises cardiac repolarization.

25. The method of claim 22, wherein the visual representation of estimated cardiac activity data for the subject is used to guide ablation of cardiac arrhythmias.

26. The method of claim 22, wherein the visual representation of estimated cardiac activity data for the subject is used to guide cardiac synchronized therapy.

* * * * *

UNITED STATES PATENT AND TRADEMARK OFFICE
CERTIFICATE OF CORRECTION

PATENT NO. : 7,841,986 B2
APPLICATION NO. : 11/747161
DATED : November 30, 2010
INVENTOR(S) : Bin He, Zhongming Liu and Chenguang Liu It is certified that error appears in the above-identified patent and that said Letters Patent is hereby corrected as shown below:

In the Claims:

Column 28, line 29, in Claim 22, after "portion" delete "while".

Signed and Sealed this
First Day of March, 2011

David J. Kappos
*Director of the United States Patent and Trademark Office*